United States Patent [19]
Fujita et al.

[11] Patent Number: 5,554,316
[45] Date of Patent: Sep. 10, 1996

[54] HEXENEDIYNE DERIVATIVE AND A LIQUID CRYSTAL COMPOSITION

[75] Inventors: Atsuko Fujita; Shuichi Matsui; Kazutoshi Miyazawa; Yasuyuki Goto; Etsuo Nakagawa; Shinichi Sawada, all of Chibaken, Japan

[73] Assignee: Chisso Corporation, Osaka, Japan

[21] Appl. No.: 403,615

[22] Filed: Mar. 14, 1995

[30] Foreign Application Priority Data

Mar. 16, 1994 [JP] Japan ..................... 6-072613

[51] Int. Cl.$^6$ .............. C09K 19/52; C09K 19/34; C07C 22/08; C07C 43/215; C07C 43/225
[52] U.S. Cl. .............. 252/299.01; 252/299.61; 359/103; 568/631; 568/634; 568/669; 570/128
[58] Field of Search ............ 252/299.01, 299.61; 359/103; 568/631, 634, 669; 570/128

[56] References Cited

FOREIGN PATENT DOCUMENTS

| 1-502823 | 9/1989 | Japan . |
| 3-294386 | 12/1991 | Japan . |
| 5-281147 | 11/1994 | Japan . |

OTHER PUBLICATIONS

"Diacetylenic Liquid Crystals", *Mol. Cryst. Liq. Cryst.*, 1978, vol. 48, pp. 175–182.
"Derivative des Stilbens," Fluessigkeltekristalle, Fluessige Kristallen, Leipzig VEB Deutcher Verlag fuer Grundstoff Industrie, 1975, 49.
CA 113: 242024, 1990.
Journal of Organic Chemistry, vol. 59, No. 23, 1994 Easton US, pp. 7142–7143, B. Konig et al. "Synthesis and Photo-induced cis–trans of Diaryl Enediyne Chromophores".

Primary Examiner—Shean C. Wu
Attorney, Agent, or Firm—Lowe, Price, LeBlanc & Becker

[57] ABSTRACT

A novel compound having superior characteristics as a liquid crystal material and having a good stability under usual use environment, and a composition having improved viscosity, optical anisotropy and other properties, and further a liquid crystal display element are provided, the compound being a hexenediyne compound expressed by the formula

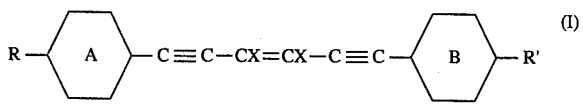

wherein R and R' each represent an alkyl group or an alkoxy group, independently of each other; rings A and B each represent 1,4-cyclohexylene or 1,4-phenylene; and X represents H or F), and particularly when fluorine atom is introduced into the central part of the molecule of the compound, the viscosity is notably lowered; and when a liquid crystal composition is composed of the compound as its component, the operation temperature range of the liquid crystal composition is broadened, and the high speed response becomes possible due to the viscosity reduction, and when the cell thickness is reduced, a good display can be realized.

20 Claims, No Drawings

HEXENEDIYNE DERIVATIVE AND A LIQUID CRYSTAL COMPOSITION

BACKGROUND OF THE INVENTION

1. Field of the Invention

This invention relates to a novel liquid crystalline compound expressed by the formula (I)

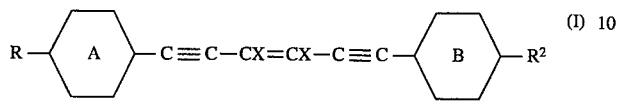

wherein $R^1$ and $R^2$ each represent an alkyl group or an alkoxy group independently of each other; ring A and ring B each represent 1,4-cyclohexylene or 1,4-phenylene independently of each other; and X represents a hydrogen atom or a fluorine atom, and a liquid crystal composition containing at least one member of said compound of the formula (I) and further, its use. The compound of the formula (I) is a useful compound as a liquid crystal material containing a conjugated hexenediene inside its molecule. 2. Detailed Description of the Related Art Liquid crystal display elements making use of characteristics such as optical anisotropy, dielectric anisotropy, etc. of liquid crystal substances have been broadly applied to watches, electronic calculators, etc. Liquid crystal phases include nematic phase, smectic phase and cholesteric phase, but nematic phase is practically most general. Display mode in this case includes those of TN (twist nematic) type, DS (dynamic scattering) type, guest-host type, DAP (deformation of aligned phases) type, etc. A number of liquid crystalline compounds used therefor have so far been developed, but any example wherein only a single compound has been filled in a display element and practically used, has not yet been found. As liquid crystal materials for display elements, it is necessary to exhibit liquid crystal phases in a broad temperature range around room temperature, be stable to moisture, light, air, etc. and to electric field and electromagnetic irradiation in the environment where they are used, and have physical properties sufficient to drive the display elements.

However, these conditions cannot be satisfied by only a single compound. Thus, several kinds of liquid crystal-line compounds have been mixed and further, non-liquid crystalline compounds have been mixed, whereby compositions according with such conditions have been prepared and practically used.

The values of physical properties such as those of optical anisotropy, dielectric anisotropy, electric conductivity, etc. sought for liquid crystal compositions depend upon display mode and shape of element. Among the values of the properties, the optical anisotropy value (Δn) of display materials requires a definite value, depending upon the cell thickness (d). For recent display elements, a method of reducing the value (d) to thereby obtain a high quality display having no domain, has been employed. Thus, in order to adjust the Δn value of liquid crystal compositions to an optimum value, liquid crystalline compounds having a large Δn value have become an important key to the above adjustment.

As compounds having a large Δn value, the following compounds have so far been generally known:

a tolan derivative (e.g. a tolan derivative disclosed in Japanese patent gazette laid-open No. Hei 01-502823; see chemical formula 11 mentioned below, or a butadiyne derivative (e.g. Mol. Cryst. Liq. Cryst. 48, 175 (1978); see chemical formula 12 mentioned below). But the former compound has a drawback of a narrow liquid crystal temperature range and the latter compound has a drawback of thermal unstability. Thus, both of the materials cannot be regarded as sufficient for achieving the above object.

Further, a stilbene derivative already known as a compound (e.g. a stilbene derivative disclosed in Flüssige Kristallen. Leipzig. VEB Deutcher Verlag für Grundstoff Industrie, 1975, 49 : see chemical Formula 13 mentioned below), and a difluorostilbene recently developed in order to stabilize it (e.g. difluorostilbene derivative disclosed in Official Gazette of Japanese patent application laid-open No. Hei 03-294386: see chemical formula 14, mentioned below) are also useful as a liquid crystal material having a relatively large Δn and low viscosity, but either of the derivatives have no sufficiently broad liquid crystal temperature range; hence in order to overcome this defect, they could not have helped being used in admixture with other liquid crystal materials having a high clearing point. In order to develop novel compounds overcoming the drawbacks of these materials, the present inventors have completed a compound having an enyne structure conjugated within its inner part (an enyne derivative disclosed in Japanese patent application No. Hei 05-281147; see the following (chemical formula 15):

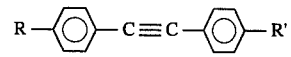

(chemical formula 11)

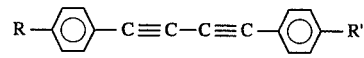

(chemical formula 12)

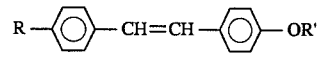

(chemical formula 13)

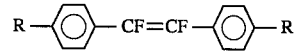

(chemical formula 14)

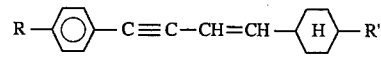

(chemical formula 15)

However, it is also difficult to regard the last-mentioned compound as exhibiting a sufficiently large Δn value. Thus, it has been long desired to develop a novel material having a very large Δn value, a broad liquid crystal temperature range, having a good compatibility with other liquid crystal materials, a low viscosity and a high reliability.

PROBLEM TO BE SOLVED BY THE INVENTION

The present inventors have made extensive research in order to solve the above problems, and as a result, have found a compound having a novel structure expressed by the above formula (I) and also having improved characteristics as compared with those of generally known compounds, and have completed the present invention. As apparent from the foregoing, the object of the present invention is to provide a liquid crystal material as desired as above and its use application (liquid crystal composition).

MEANS FOR SOLVING THE PROBLEM

The present invention has the following constitutions (1) to (17):

(1) A hexenediyne having the following formula (I):

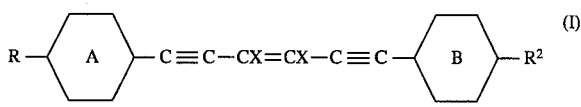

wherein $R^1$ and $R^2$ each represent an alkyl group or an alkoxy group independently of each other; ring A and ring B each represent 1,4-cyclohexylene or 1,4-phenylene independently of each other; and X represents hydrogen atom or fluorine atom.

(2) A compound according to item (1) wherein ring A represents 1,4-cyclohexylene.

(3) A compound according to item (1) wherein ring A represents 1,4-phenylene and X represents hydrogen atom.

(4) A compound according to item (1) wherein ring A represents 1,4-phenylene and X represents fluorine atom.

(5) A compound according to item (3) wherein ring B represents 1,4-phenylene.

(6) A compound according to item (3) wherein $R^1$ and $R^2$ each represent an alkyl group of 1 to 10 carbon atoms and ring B represents 1,4-phenylene.

(7) A compound according to item (3) wherein $R^1$ represents an alkoxy group of 1 to 10 carbon atoms; $R^2$ represents an alkyl group of 1 to 10 carbon atoms; and ring B represents 1,4-phenylene.

(8) A compound according to item (3) wherein ring B represents 1,4-cyclohexylene.

(9) A compound according to item (2) wherein ring B represents 1,4-cyclohexylene and X represents hydrogen atom.

(10) A compound according to item (4) wherein ring B represents 1,4-phenylene.

(11) A compound according to item (4) wherein $R^1$ and $R^2$ each represent an alkyl group of 1 to 10 carbon atoms and ring B represents 1,4-phenylene.

(12) A compound according to item (4) wherein $R^1$ represents an alkoxy group of 1 to 10 carbon atoms; $R^2$ represents an alkyl group of 1 to 10 carbon atoms; and ring B represents 1,4-phenylene.

(13) A liquid crystal composition which is characterized by containing at least one kind of liquid crystalline compounds expressed by the formula I of the item (1).

(14) A liquid crystal composition which is characterized by containing as a first component, at least one kind of compounds of items (1) to (12), and as a second component, at least one kind of compounds selected from the group consisting of those expressed by the following formulas II, III and IV:

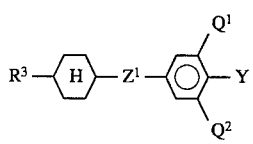

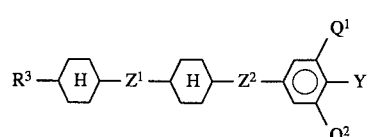

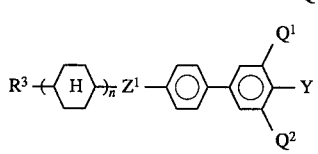

wherein $R^3$ represents an alkyl group of 1 to 10 carbon atoms; Y represents F or Cl; $Q^1$ and $Q^2$ each represent H or F independently of each other; n represents 1 or 2; and $Z^1$ and $Z^2$ each represent —$CH_2CH_2$— or covalent bond, independently of each other.

(15) A liquid crystal composition which is characterized by containing as a first component, at least one kind of compounds described in items 1 to 12, and as a second component, at least one kind of compounds selected from the group consisting of those expressed by the folloiwng formulas V, VI, VII, VIII and IX:

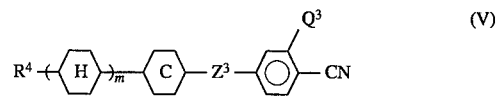

wherein $R^4$ represents an alkyl group of 1 to 10 carbon atoms or an alkenyl group of 2 to 10 carbon atoms, and in either of the groups, optional methylene groups (—$CH_2$—) may be replaced by oxygen atom (—O—), but two or more methylene groups should not be continuedly replaced by oxygen atom; $Z^3$ represents —$CH_2CH_2$—, —COO— or covalent bond; $Q^3$ represents H or F; ring C represents 1,4-cyclohexylene, 1,4-phenylene or 1,3-dioxane-2,5-diyl; and m represents 0 or 1,

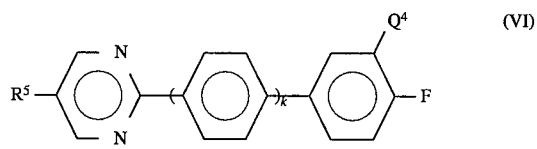

wherein $R^5$ represents an alkyl group of 1 to 10 carbon atoms; $Q^4$ represents H or F; and K represents 0 or 1,

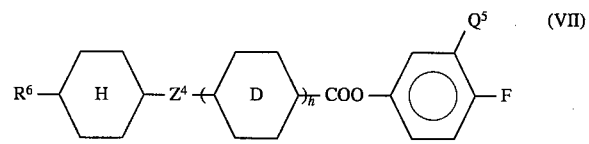

wherein $R^6$ represents an alkyl group of 1 to 10 carbon atoms; ring D represents 1,4-cyclohexylene or 1,4-phenylene; $Q^5$ represents H or F; $Z^4$ represents —COO— or covalent bond; and h represents 0 or 1,

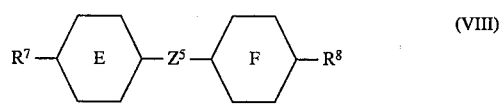

wherein $R^7$ and $R^8$ each represent an alkyl group of 1 to 10 carbon atoms or an alkenyl group of 2 to 10 carbon atoms, independently of each other, and in either groups, optional methylene groups (—$CH_2$—) may be replaced by oxygen atom, but two or more methylene groups should not be continuedly replaced by oxygen atom; ring E represents 1,4-cyclohexylene, 1,3-pyrimidine-2,5-diyl or 1,4-phenylene; ring F represents 1,4-cyclohexylene or 1,4-phenylene, and $Z^5$ represents —C≡C—, —COO—, —$CH_2CH_2$— or covalent bond, and

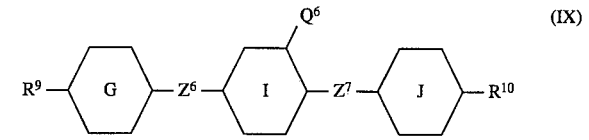

wherein $R^9$ represents an alkyl group or an alkyloxy group, each of 1 to 10 carbon atoms; $R^{10}$ represents an alkyl group, an alkyloxy group or an alkyloxymethyl group, each 1 to 10 carbon atoms; ring G represents 1,4-cyclohexylene or 1,3-pyrimidine-2,5-diyl; ring I and ring J each represent 1,4- cyclohexylene or 1,4-phenylene, independently of each other, $Z^6$ represents —COO—, —CH$_2$CH$_2$— or covalent bond; $Z^7$ represents —C≡C—, —COO— or covalent bond; and $Q^6$ represents H or F.

(16) A liquid crystal composition which is characterized by containing as a first component, at least one kind of compounds according to items 1 to 12, as a second component, at least one compound chosen from among those expressed by the formulas II, III and IV set forth in item 14, and as a third component, at least one compound chosen from among those expressed by the formulas V, VI, VII, VIII and IX set forth in item 15.

(17) A liquid crystal display element using either one of liquid crystal compositions set forth in items 13 to 16.

The constitution and effectiveness of the present invention will be described below in more detail.

The compounds expressed by the formula (I) of the present invention can be concretely represented by the compounds of the formulas I-A to I-F wherein $R^1$ and $R^2$ each represent an alkyl group or an alkoxy group independently of each other and X represents F.

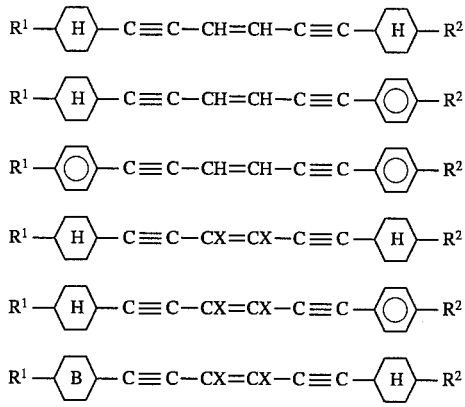

As preferable compounds among those of the formulas (I-A) to (I-F), the following compounds (I-a to I-g) can be illustrated:

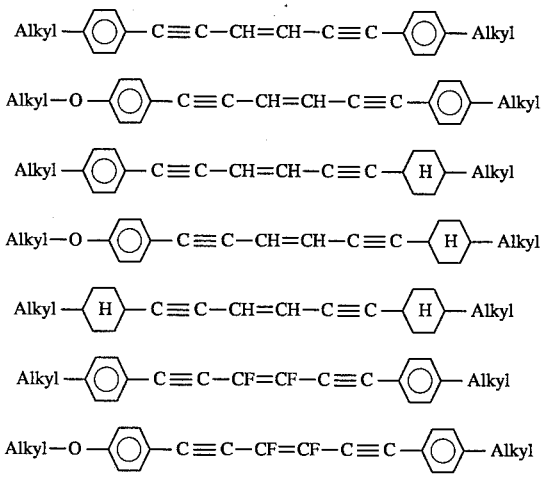

Among these compounds of the present invention, those having two aromatic rings and highly conjugated, I-a, I-b, I-f and I-g, are useful compounds having an incomparably large Δn value and a broad liquid crystal temperature range. Further, compounds having an alkoxy group at their molecular terminal, I-b, I-d and I-g have a broader liquid crystal temperature range than those of compounds replaced by an alkyl group. Further, since compounds of I-c, I-d and I-e have a cylcohexane ring, they exhibit an improved compatibility and hence are useful. Further, compounds of I-f and I-g having a difluorohexenediyne chain exhibit a specifically low viscosity and also have a large Δn value and a broad liquid crystal temperature range.

At that time, $R^1$ and $R^2$ each are preferred to be a linear chain alkyl group of 7 or less carbon atoms in the aspect that the temperature range of the nematic liquid crystal is broad. Further, the compound of the present invention has two isomers of E-form and Z-form originated from the double bond at the central portion having a hexenediyne structure specific of the compound, and the isomer of E-form can afford a more useful liquid crystalline compound.

The liquid crystal composition of the present invention contains at least one kind of the liquid crystalline compound expressed by the formula (I). This liquid crystal composition is preferred to contain at least one kind of the compound expressed by the formula (I) in an optional ratio, for exhibiting superior characteristics. Further, it is preferred to contain at least one kind of the compound of the formula (I) in a ratio of 0.1 to 40% by weight.

The liquid crystal composition of the present invention may contain as a first component, at least one kind of compounds of the formula (I) and as a second component, at least one kind of compounds selected from those expressed by the following formulas (II), (III) and (IV):

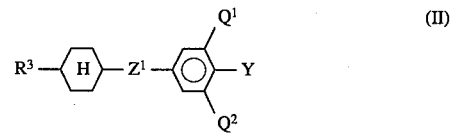

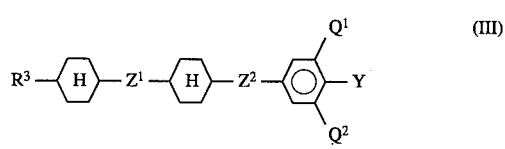

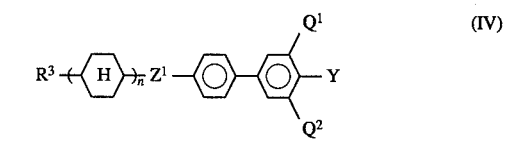

wherein $R^3$ represents an alkyl group of 1 to 10 carbon atoms; Y represents F or Cl; $Q^1$ and $Q^2$ each represent H or F independently of each other; n represents 1 or 2; and $Z^1$ and $Z^2$ each represent —CH$_2$CH$_2$— or covalent bond, independently of each other.

As the compounds of the formulas II to IV used in the present invention, the following compounds can be preferably enumerated:

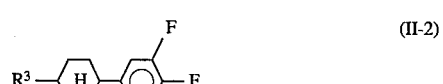

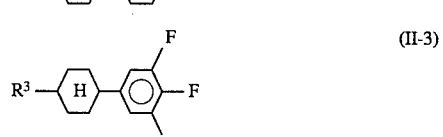

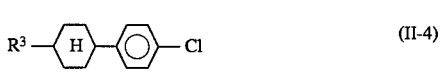

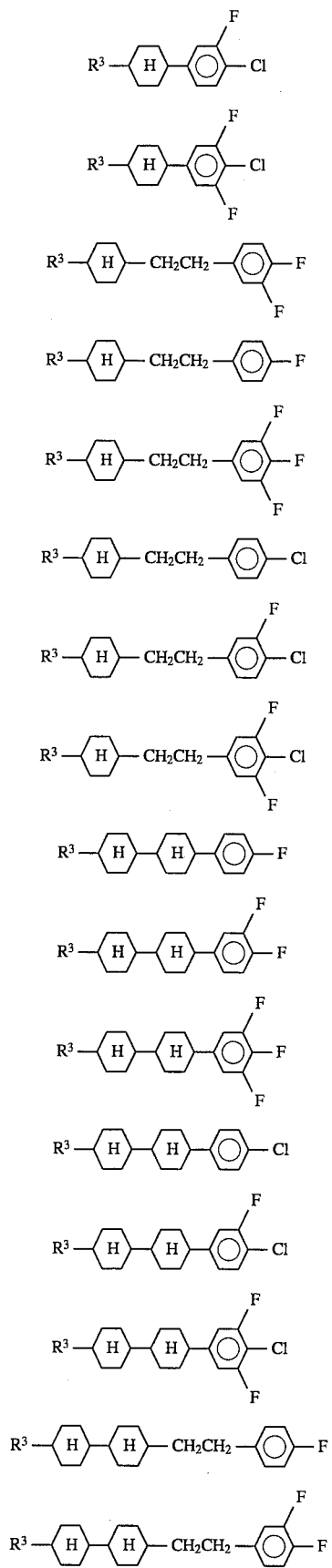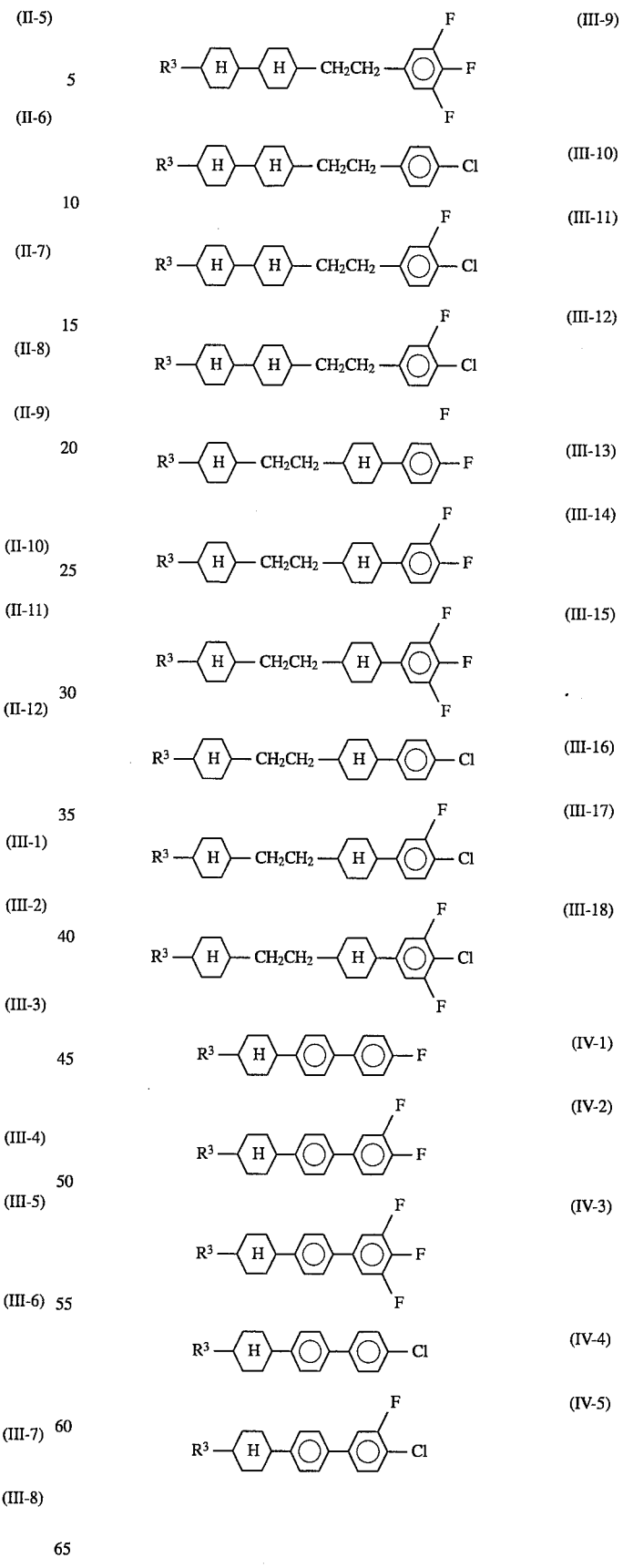

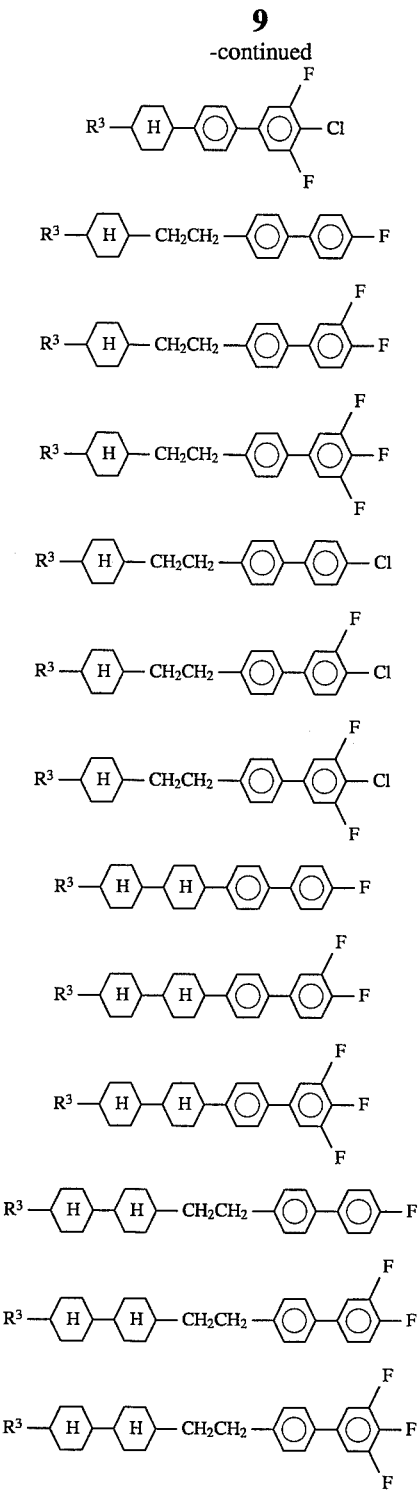

wherein R³ represents an alkyl group.

Compounds expressed by the formulas (II) to (IV) have a positive dielectric anisotropy, a far superior thermal stability and chemical stability, and they are useful for preparing a liquid crystal composition for TFT (AM-LCD) for which a high reliability upon e.g. a high voltage retention, a large specific resistivity, etc. are particularly required.

The used quantity of the compounds expressed by the formulas II–IV is employed within an optional range, but preferably in 10 to 97% by weight, more preferably in 40 to 95% by weight.

Further, the liquid crystal composition of the present invention contains as a first component, at least one kind of the compound of the formula (I) and in addition, as a second component, at least one kind selected from compounds expressed by the following formulas V, VI, VII, VIII and IX:

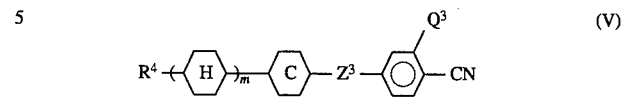

wherein R⁴ represents an alkyl group of 1 to 10 carbon atoms or an alkenyl group of 2 to 10 carbon atoms; in either case, an optional methylene group (—CH₂—) therein may be replaced by —O—, but two or more methylene groups should not be continuedly replaced by —O—; Z³ represents —CH₂CH₂—, —COO— or covalent bond; Q³ represents H or F; ring C represents 1,4-cyclohexylene, 1,4-phenylene or 1,3-dioxane-2,5-diyl; m represents 0 or 1,

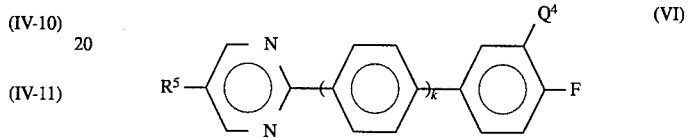

wherein R⁵ represents an alkyl group of 1 to 10 carbon atoms; Q⁴ represents H or F; and k represents 0 or 1,

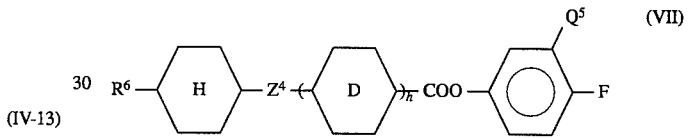

wherein R⁶ represents an alkyl group of 1 to 10 carbon atoms; ring D represents 1,4-cyclohexylene or 1,4-phenylene; Q⁵ represents H or F; Z⁴ represents —COO— or covalent bond; and h represents 0 or 1,

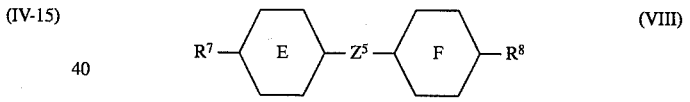

wherein R⁷ and R⁸ each represent an alkyl group of 1 to 10 carbon atoms or an alkenyl group of 2 to 10 carbon atoms independently of each other; in either case, an optional methylene group (—CH₂—) may be replaced by —O—, but two or more methylene groups should not be continuedly replaced by —O—; ring E represents 1,4-cyclohexylene, 1,3-pyrimidine-2,5-diyl or 1,4-phenylene; ring F represents 1,4-cyclohexylene or 1,4-phenylene; and Z⁵ represents —C≡C—, —COO—, —CH₂CH₂— or covalent bond,

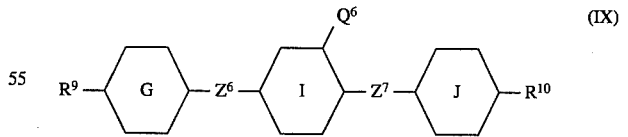

wherein R⁹ represents an alkyl group or alkoxy group of 1 to 10 carbon atoms; R¹⁰ represents an alkyl group, an alkoxy group or an alkoxymethyl group of 1 to 10 carbon atoms; ring G represents 1,4-cyclohexylene or 1,3-pyrimidine-2,5-diyl; rings I and J each represent 1,4-cyclohexylene or 1,4-phenylene independently of each other; Z⁶ represents —COO—, —CH₂CH₂— or covalent bond; Z⁷ represents —C≡C—, —COO— or covalent bond; and Q⁶ represents H or F.

As compounds expressed by the formulas (V) to (VII), the following compound can be preferably illustrated:
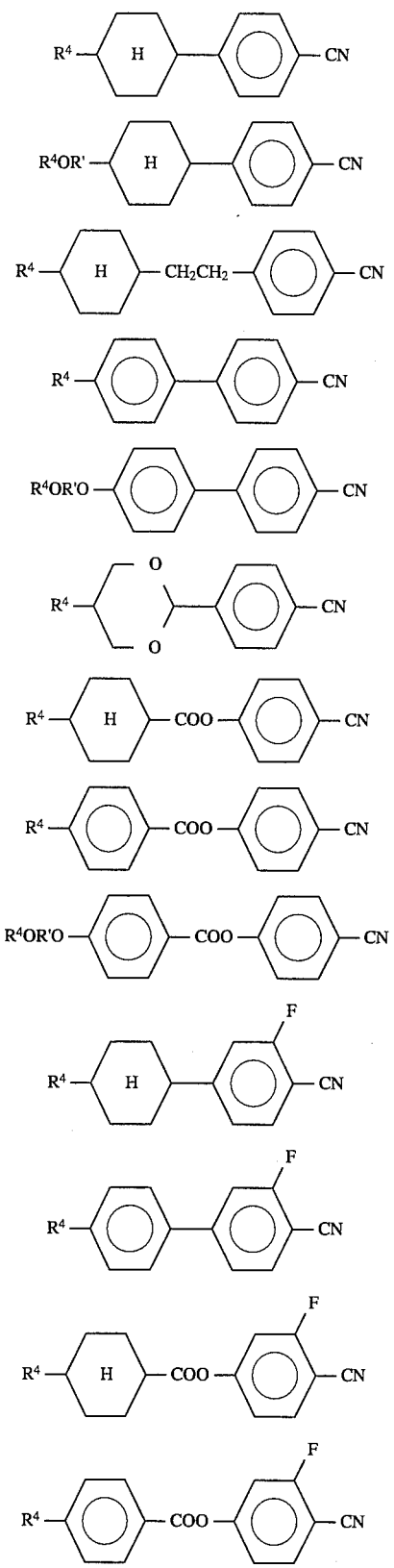
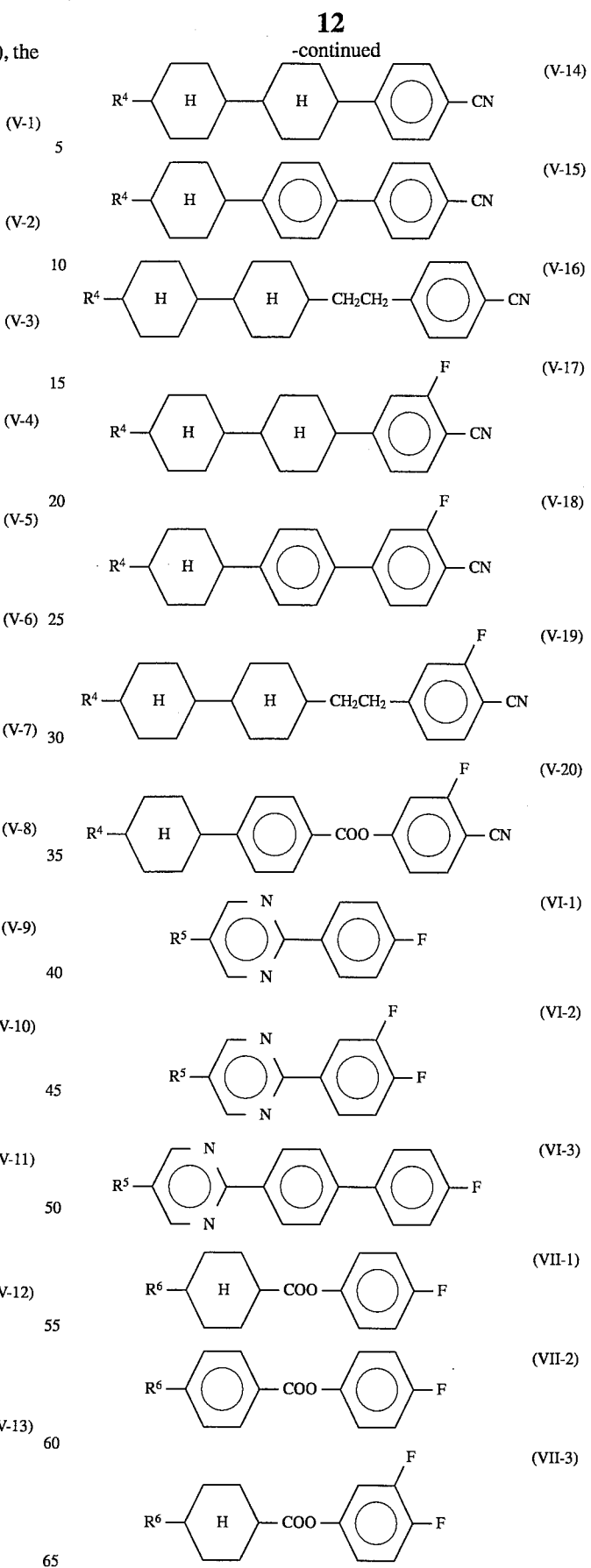

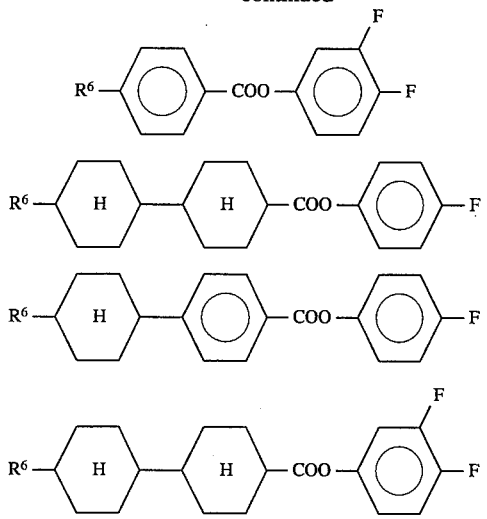

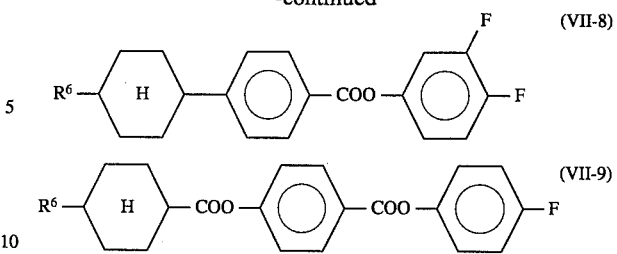

wherein $R^4$, $R^5$ and $R^6$ each represent an alkyl group or an alkenyl group and $R^7$ represents an alkylene.

The compounds of the formulas V to VII have a large, positive dielectric anisotropy value and are used particularly for reducing the threshold voltage. Further, they are also used for adjusting the viscosity or Δn value or for broadening the nematic temperature range by raising the clearing point, etc. and they are used for improving the steepness.

As the compounds of the formulas VIII and IX, the following compounds can be preferably illustrated:

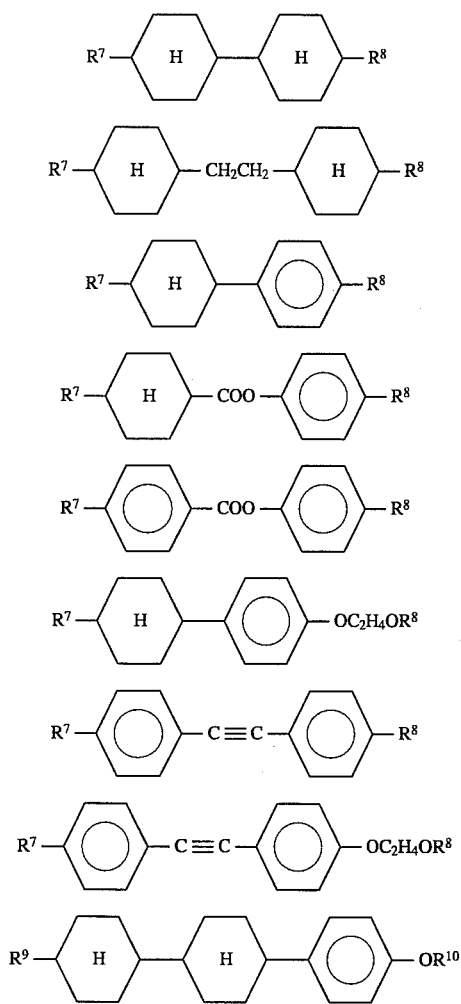

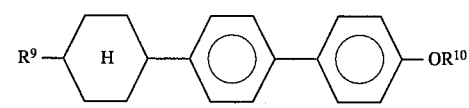 (IX-4)

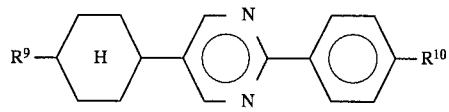 (IX-5)

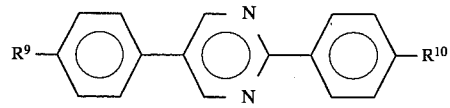 (IX-6)

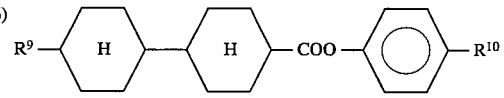 (IX-7)

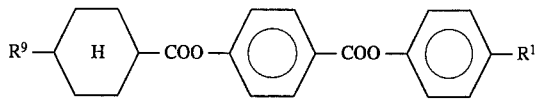 (IX-8)

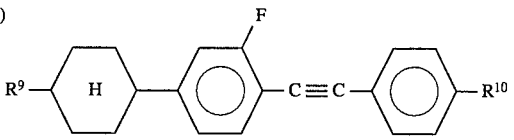 (IX-9)

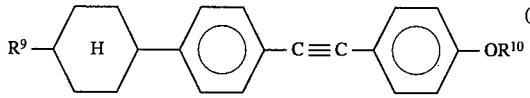 (IX-10)

(IX-11)

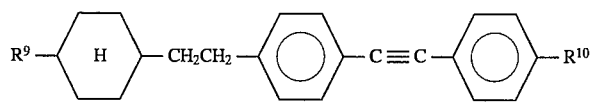 (IX-12)

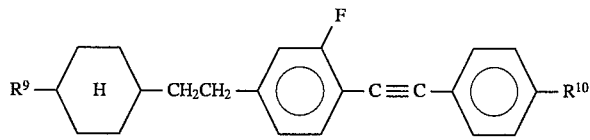 (IX-13)

wherein $R^7$, $R^8$, $R^9$ and $R^{10}$ each represent an alkyl group.

The compounds of the formulas VIII and IX each exhibit a negative or positive small dielectric anisotropy value. The compounds of the formula VIII are used mainly for reducing the viscosity or adjusting the Δn value or used for both the objects. Further, the compounds of the formula IX are used for broadening the nematic range e.g. by raising the clearing point or for adjusting the Δn value, or for achieving both the obsects. Thus, the compounds of the formulas V to IX are useful for preparing the liquid crystal compositions particularly in STN display mode or TN display mode. As to the used quantity of the compounds of the formulas V to IX, when the liquid crystal compositions for TN display mode and STN display mode are prepared, the quantity can be employed within an optional range depending upon the object, but it is preferably 10 to 97% by weight and more preferably 40 to 95% by weight.

Further, when liquid crystal compositions for TFT are prepared, it is also possible to blend with a mixture containing as a first component, at least one kind of compounds of the formula I and as a second component, at least one kind of compounds selected from the group consisting of those of the formulas II to IV, as a third component, at least one kind of compounds selected from the group consisting of those of the formulas V to IX. On the other hand, when liquid crystal compositions for STN display mode or TN display mode are prepared, it is also possible to blend with a mixture containing as a first component, at least one kind of compounds of the formula I and as a second component, at least one kind of compounds selected from the group consisting of those of the formulas V to IX, as a third component, at least one kind of compounds selected from the group consisting of those of the formulas II to IV.

In any compositions of the present invention, when at least one kind of compounds of the first component of the present invention is used, it has become possible to easily adjust the optical anisotropy, the liquid crystal temperature range, the viscosity, etc. and also to prepare a composition having a high optical anisotropy.

In the liquid crystal composition of the present invention, it is possible to contain besides the compounds expressed by the formulas I to IX, other known compounds in suitable quantities in order to adjust the threshold voltage, liquid crystal temperature range, Δn, dielectric anisotropy, viscosity, etc., in accordance with the object of liquid crystal display element used. As examples of such compounds, the following compounds can be mentioned:

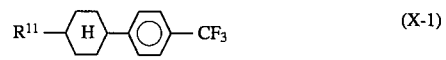 (X-1)

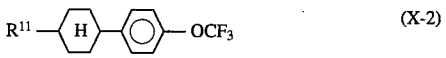 (X-2)

 (X-3)

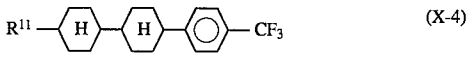 (X-4)

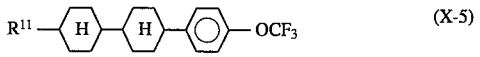 (X-5)

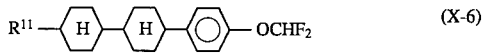 (X-6)

 (X-7)

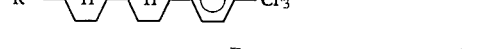 (X-8)

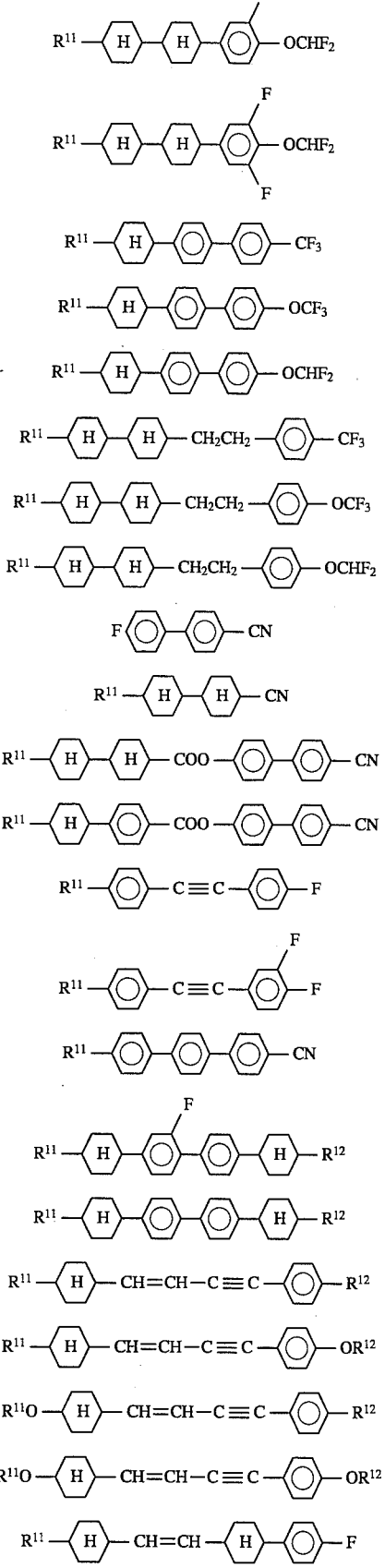

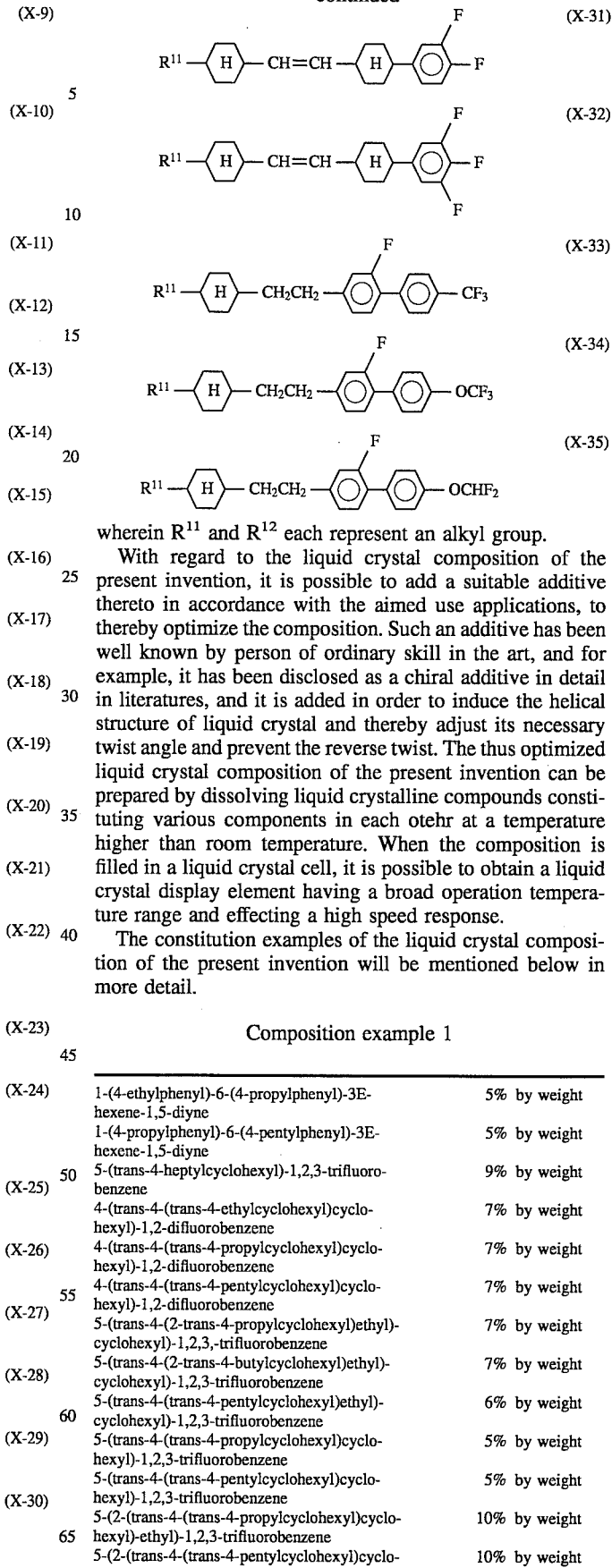

wherein $R^{11}$ and $R^{12}$ each represent an alkyl group.

With regard to the liquid crystal composition of the present invention, it is possible to add a suitable additive thereto in accordance with the aimed use applications, to thereby optimize the composition. Such an additive has been well known by person of ordinary skill in the art, and for example, it has been disclosed as a chiral additive in detail in literatures, and it is added in order to induce the helical structure of liquid crystal and thereby adjust its necessary twist angle and prevent the reverse twist. The thus optimized liquid crystal composition of the present invention can be prepared by dissolving liquid crystalline compounds constituting various components in each otehr at a temperature higher than room temperature. When the composition is filled in a liquid crystal cell, it is possible to obtain a liquid crystal display element having a broad operation temperature range and effecting a high speed response.

The constitution examples of the liquid crystal composition of the present invention will be mentioned below in more detail.

Composition example 1

| | |
|---|---|
| 1-(4-ethylphenyl)-6-(4-propylphenyl)-3E-hexene-1,5-diyne | 5% by weight |
| 1-(4-propylphenyl)-6-(4-pentylphenyl)-3E-hexene-1,5-diyne | 5% by weight |
| 5-(trans-4-heptylcyclohexyl)-1,2,3-trifluorobenzene | 9% by weight |
| 4-(trans-4-(trans-4-ethylcyclohexyl)cyclohexyl)-1,2-difluorobenzene | 7% by weight |
| 4-(trans-4-(trans-4-propylcyclohexyl)cyclohexyl)-1,2-difluorobenzene | 7% by weight |
| 4-(trans-4-(trans-4-pentylcyclohexyl)cyclohexyl)-1,2-difluorobenzene | 7% by weight |
| 5-(trans-4-(2-trans-4-propylcyclohexyl)ethyl)-cyclohexyl)-1,2,3,-trifluorobenzene | 7% by weight |
| 5-(trans-4-(2-trans-4-butylcyclohexyl)ethyl)-cyclohexyl)-1,2,3-trifluorobenzene | 7% by weight |
| 5-(trans-4-(trans-4-pentylcyclohexyl)ethyl)-cyclohexyl)-1,2,3-trifluorobenzene | 6% by weight |
| 5-(trans-4-(trans-4-propylcyclohexyl)cyclohexyl)-1,2,3-trifluorobenzene | 5% by weight |
| 5-(trans-4-(trans-4-pentylcyclohexyl)cyclohexyl)-1,2,3-trifluorobenzene | 5% by weight |
| 5-(2-(trans-4-(trans-4-propylcyclohexyl)cyclohexyl)-ethyl)-1,2,3-trifluorobenzene | 10% by weight |
| 5-(2-(trans-4-(trans-4-pentylcyclohexyl)cyclo- | 10% by weight |

Composition example 2

| | |
|---|---|
| 3,4-difluoro-1,6-di(4-propylphenyl)-3E-hexene-1,5-diyne | 6% by weight |
| 1-(4-ethylphenyl)-6-(4-propylphenyl)-3E-hexene-1,5-diyne | 5% by weight |
| 4-(trans-4-pentylcyclohexyl)chlorobenzene | 5% by weight |
| 4-(trans-4-heptylcyclohexyl)chlorobenzene | 5% by weight |
| 4-(2-(trans-4-propylcyclohexyl)ethyl)-cyclohexyl)-1,2-difluorobenzene | 10% by weight |
| 4-(trans-4-(2-(trans-4-butylcyclohexyl)ethyl)-cyclohexyl-1,2-difluorobenzene | 5% by weight |
| 4-(trans-4-(2-(trans-4-pentylcyclohexyl)ethyl)-cyclohexyl)-1,2-difluorobenzene | 10% by weight |
| 4-(trans-4-(trans-4-ethylcyclohexyl)cyclohexyl)chlorobenzene | 7% by weight |
| 4-(trans-4-(trans-4-propylcyclohexyl)cyclohexyl)chlorobenzene | 7% by weight |
| 4-(trans-4-(trans-4-pentylcyclohexyl)cyclohexyl)chlorobenzene | 7% by weight |
| 4-(trans-4-(trans-4-propylcyclohexyl)cyclohexyl)fluorobenzene | 4% by weight |
| 4-(4-(trans-4-propylcyclohexyl)phenyl)fluorobenzene | 5% by weight |
| 4-(4-(trans-4-ethylcyclohexyl)phenyl)-1,2-difluorobenzene | 6% by weight |
| 4-(4-(trans-4-propylcyclohexyl)phenyl)-1,2-difluorobenzene | 6% by weight |
| 4-(4-(trans-4-pentylcyclohexyl)phenyl)-1,2-difluorobenzene | 12% by weight |

Composition example 3

| | |
|---|---|
| 3,4-difluoro-1,6-di(4-propylphenyl)-3E-hexene-1,5-diyne | 8% by weight |
| 1-(4-propylphenyl)-6-(trans-4-pentylcyclohexyl)-3E-hexene-1,5-diyne | 7% by weight |
| 4-(2-(trans-4-pentylcyclohexyl)ethyl)-1,2-difluoridebenzene | 5% by weight |
| 4-(trans-4-(trans-4-ethylcyclohexyl)cyclohexyl)-1,2-difluorobenzene | 6% by weight |
| 4-(trans-4-(trans-4-propylcyclohexyl)cyclohexyl)-1,2-difluorobenzene | 6% by weight |
| 4-(trans-4-(trans-4-pentylcyclohexyl)cyclohexyl)-1,2-difluorobenzene | 6% by weight |
| 3,4-difluoro-4'-(trans-4-ethylcyclohexyl)-biphenyl | 5% by weight |
| 3,4-difluoro-4'-(trans-4-propylcyclohexyl)-biphenyl | 5% by weight |
| 3,4-difluoro-4'-(trans-4-pentylcyclohexyl)-biphenyl | 10% by weight |
| 4-(trans-4-(2-(trans-4-ethylcyclohexyl)ethyl)-cyclohexyl)-1,2-difluorobenzene | 10% by weight |
| 4-(trans-4-(2-trans-4-propylcyclohexyl)ethyl)-cyclohexyl)-1,2-difluorobenzene | 5% by weight |
| 4-(trans-4-(2-trans-4-pentylcyclohexyl)ethyl)-cyclohexyl)-1,2-difluorobenzene | 10% by weight |
| 4-fluorophenyl trans-4-pentylcyclohexanecarboxylate | 6% by weight |
| 4-fluorophenyl trans-4-heptylcyclohexanecarboxylate | 6% by weight |
| 4-(trans-4-(trans-4-propylcyclohexyl)cyclohexyl)toluene | 5% by weight |
| hexyl)ethyl)-1,2,3-trifluorobenzene | |
| 3,4,5-trifluoro-4'-(trans-4-propylcyclohexyl)-biphenyl | 5% by weight |
| 3,4,5-trifluoro-4'-(trans-4-pentylcyclohexyl)-biphenyl | 5% by weight |

Composition example 4

| | |
|---|---|
| 1-(4-ethylphenyl)-6-(4-propoxyphenyl)-3E-hexene-1,5-diyne | 5% by weight |
| 1-(4-pentylphenyl)-6-(4-propoxyphenyl)-3E-hexene-1,5-diyne | 5% by weight |
| 4-(trans-4-(trans-4-ethylcyclohexyl)cyclohexyl)-1,2-difluorobenzene | 10% by weight |
| 4-(trans-4-(trans-4-propylcyclohexyl)cyclohexyl)-1,2-difluorobenzene | 10% by weight |
| 4-(trans-4-(trans-4-pentylcyclohexyl)cyclohexyl)-1,2-difluorobenzene | 10% by weight |
| 3,4-difluoro-4'-(trans-4-ethylcyclohexyl)biphenyl | 5% by weight |
| 3,4-difluoro-4'-(trans-4-propylcyclohexyl)biphenyl | 5% by weight |
| 3,4-difluoro-4'-(trans-4-pentylcyclohexyl)biphenyl | 10% by weight |
| 1-chloro-2-fluoro-4-(trans-4-(2-(trans-4-propylcyclohexyl)ethyl)cyclohexyl)benzene | 5% by weight |
| 1-chloro-2-fluoro-4-(trans-4-(2-(trans-4-pentylcyclohexyl)ethyl)cyclohexyl)benzene | 5% by weight |
| 5-(trans-4-(trans-4-propylcyclohexyl)cyclohexyl)-1,2,3-trifluorobenzene | 7% by weight |
| 5-(trans-4-(trans-4-pentylcyclohexyl)cyclohexyl)-1,2,3-trifluorobenzene | 7% by weight |
| 3,4,5-(trifluoro-4'-(trans-4-propylcyclohexyl)-biphenyl | 8% by weight |
| 3,4,5-trifluoro-4'-(trans-4-pentylpropylcyclohexyl)biphenyl | 8% by weight |

Composition example 5

| | |
|---|---|
| 1-(4-ethylphenyl)-6-(4-propylphenyl)-3E-hexene-1,5-diyne | 8% by weight |
| 4-ethyl-4'-cyanobiphenyl | 8% by weight |
| 4-pentyl-4'-cyanobiphenyl | 8% by weight |
| 4-(trans-4-methoxymethylcyclohexyl)benzonitrile | 10% by weight |
| 4-(trans-4-propylcyclohexyl)benzonitrile | 10% by weight |
| trans-4-(trans-4-methoxymethylcyclohexyl)-pentylcyclohexane | 5% by weight |
| 2-(4-ethylphenyl)-5-ethyl-1,3-pyrimidine | 4% by weight |
| 2-(4-ethylphenyl)-5-propyl-1,3-pyrimidine | 4% by weight |
| 2-(4-ethylphenyl)-5-butyl-1,3-pyrimidine | 4% by weight |
| 2-(4-(trans-4-propylcyclohexyl)phenyl)-5-ethyl-1,3-pyrimidine | 7% by weight |
| 2-(4-(trans-4-propylcyclohexyl)phenyl)-5-propyl-1,3-pyrimidine | 7% by weight |
| 4-(trans-4-(trans-4-propylcyclohexyl)cyclohexyl)toluene | 8% by weight |
| 4-(trans-4-(trans-4-propylcyclohexyl)cyclohexyl)anisole | 5% by weight |
| 4-(trans-4-(trans-4-ethylcyclohexyl)cyclohexyl)-1,2-difluorobenzene | 4% by weight |
| 4-(trans-4-(trans-4-propylcyclohexyl)cyclohexyl)-1,2-difluorobenzene | 4% by weight |
| 4-(trans-4-(trans-4-pentylcyclohexyl)cyclohexyl)-1,2-difluorobenzene | 4% by weight |

Composition example 6

| | |
|---|---|
| 1-(4-ethylphenyl)-6-(4-propoxyphenyl)-3E-hexene-1,5-diyne | 4% by weight |
| 1-(4-pentylphenyl)-6-(4-propoxyphenyl)-3E-hexene-1,5-diyne | 4% by weight |
| 1-(4-ethylphenyl)-6-(4-propylphenyl)-3E-hexene-1,5-diyne | 4% by weight |
| 4-(trans-4-(3-butenyl)cyclohexyl)benzonitrile | 8% by weight |
| 4-(trans-4-(3E-pentenyl)cyclohexyl)benzonitrile | 8% by weight |
| 4-(trans-4-ethylcyclohexyl)benzonitrile | 8% by weight |
| 4-(trans-4-propylcyclohexyl)benzonitrile | 8% by weight |
| 1-(4-ethylphenyl)-2-tolylacetylene | 4% by weight |
| 1-(4-hexylphenyl)-2-tolylacetylene | 8% by weight |

-continued

| | |
|---|---|
| 1,2-di(4-butylphenyl)acetylene | 4% by weight |
| 4-(trans-4-(trans-4-propylcyclohexyl)cyclohexyl)toluene | 5% by weight |
| 4-(trans-4-(trans-4-propylcyclohexyl)cyclohexyl)propylbenzene | 5% by weight |
| 1-(4-ethylphenyl)-2-(2-fluoro-4-(trans-4-propylcyclohexyl)phenyl)acetylene | 5% by weight |
| 1-(4-propylphenyl)-2-(2-fluoro-4-(trans-4-propylcyclohexyl)phenyl)acetylene | 5% by weight |
| 1-(4-butylphenyl)-2-(2-fluoro-4-(trans-4-propylcyclohexyl)phenyl)acetylene | 5% by weight |
| 4-fluoro-4'-(trans-4-ethylcyclohexyl)biphenyl | 5% by weight |
| 4-fluoro-4'-(trans-4-propylcyclohexyl)biphenyl | 5% by weight |
| 4-fluoro-4'-(trans-4-pentylcyclohexyl)biphenyl | 5% by weight |

Composition example 7

| | |
|---|---|
| 3,4-difluoro-1,6-di(4-propylphenyl)-3E-hexene-1,5-diyne | 7% by weight |
| 1-(trans-4-pentylcyclohexyl)-6-(4-propylphenyl)-3E-hexene-1,5-diyne | 7% by weight |
| 1-(4-ethylphenyl)-6-(4-propylphenyl)-3E-hexene-1,5-diyne | 6% by weight |
| 3-fluoro-4-(trans-4-ethylcyclohexyl)benzonitrile | 12% by weight |
| 3-fluoro-4-(trans-4-propylcyclohexyl)benzonitrile | 12% by weight |
| 4-(trans-5-butyl-1,3-dioxane-2-yl)benzonitrile | 8% by weight |
| 4-(trans-4-methoxymethylcyclohexyl)benzonitrile | 8% by weight |
| 4-butoxyphenyl trans-4-propylcyclohexanecarboxylate | 5% by weight |
| 4-ethoxyphenyl trans-4-butylcyclohexanecarboxylate | 5% by weight |
| 4-methoxyphenyl trans-4-pentylcyclohexanecarboxylate | 5% by weight |
| 4-(trans-4-(trans-4-ethylcyclohexyl)cyclohexyl)-1,2-difluorobenzene | 5% by weight |
| 4-(trans-4-(trans-4-propylcyclohexyl)cyclohexyl)-1,2-difluorobenzene | 5% by weight |
| 4-(trans-4-(trans-4-pentylcyclohexyl)cyclohexyl)-1,2-difluorobenzene | 5% by weight |
| 4-fluorophenyl 4-(trans-4-propylcyclohexyl)benzoate | 5% by weight |
| 4-(4-fluorophenyloxycarbonyl)phenyl trans-4-propyl-cyclohexanecarboxylate | 5% by weight |

Composition example 8

| | |
|---|---|
| 3,4-difluoro-1,6-di(4-propylphenyl)-3E-hexene-1,5-diyne | 6% by weight |
| 1-(trans-4-pentylcyclohexyl)-6-(4-propylphenyl)-3E-hexene-1,5-diyne | 5% by weight |
| 1-(4-ethylphenyl)-6-(4-propylphenyl)-3E-hexene-1,5-diyne | 5% by weight |
| 4-cyanophenyl 4-ethylbenzoate | 10% by weight |
| 4-cyanophenyl 4-propylbenzoate | 5% by weight |
| 2-(3,4-difluorophenyl)-5-propyl-1,3-pyrimidine | 10% by weight |
| 2-(3,4-difluorophenyl)-5-pentyl-1,3-pyrimidine | 10% by weight |
| 2-fluoro-4-(trans-4-propylcyclohexyl)benzonitrile | 5% by weight |
| 2-fluoro-4-(trans-4-(trans-4-ethylcyclohexyl)cyclohexyl)benzonitrile | 10% by weight |
| 2-fluoro-4-(trans-4-(trans-4-propylcyclohexyl)cyclohexyl)benzonitrile | 10% by weight |
| 4-fluoro-4'-(5-propyl-1,3-pyrimidin-2-yl)biphenyl | 6% by weight |
| 4-fluoro-4'-(5-butyl-1,3-pyrimidin-2-yl)biphenyl | 6% by weight |
| 4-fluorophenyl trans-4-(trans-4-propylcyclohexyl)cyclohexanecarboxylate | 6% by weight |
| 4-fluorophenyl trans-4-(trans-4-pentylcyclohexyl)cyclohexanecarboxylate | 6% by weight |

Composition example 9

| | |
|---|---|
| 1-(4-ethylphenyl)-6-(4-propoxyphenyl)-3E-hexene-1,5-diyne | 5% by weight |
| 1-(4-pentylphenyl)-6-(4-propoxyphenyl)-3E-hexene-1,5-diyne | 5% by weight |
| 4-(trans-4-(3-butenyl)cyclohexyl)benzonitrile | 10% by weight |
| 4-(trans-4-(3E-pentenyl)cyclohexyl)benzonitrile | 10% by weight |
| 4-(trans-4-propylcyclohexyl)benzonitrile | 10% by weight |
| 1-(4-ethylphenyl)-2-tolylacetylene | 5% by weight |
| 1-(4-hexylphenyl)-2-tolylacetylene | 10% by weight |
| 1,2-di(4-butylphenyl)acetylene | 5% by weight |
| 1-(4-ethylphenyl)-2-anisylacetylene | 5% by weight |
| 4-(4-propylcyclohexyl)ethoxybenzene | 5% by weight |
| 4-fluoro-4'-(5-propyl-1,3-pyrimidin-2-yl)biphenyl | 5% by weight |
| 4-fluoro-4'-(5-butyl-1,3-pyrimidin-2-yl)biphenyl | 5% by weight |
| 1-(4-ethylphenyl)-2-(2-fluoro-4-(trans-4-propylcyclohexyl)phenyl)acetylene | 4% by weight |
| 1-(4-propylphenyl)-2-(2-fluoro-4-(trans-4-propylcyclohexyl)phenyl)acetylene | 4% by weight |
| 1-(4-ethylphenyl)-2-(4-(2-(trans-4-propylcyclohexyl)ethyl)phenyl)acetylene | 4% by weight |
| 1-(4-propylphenyl)-2-(4-(2-(trans-4-propylcyclohexyl)ethyl)phenyl)acetylene | 4% by weight |
| 1-(4-butylphenyl)-2-(4-(2-(trans-4-propylcyclohexyl)ethyl)phenyl)acetylene | 4% by weight |

Composition example 10

| | |
|---|---|
| 1-(4-ethylphenyl)-6-(4-propylphenyl)-3E-hexene-1,5-diyne | 7% by weight |
| 1-(4-propylphenyl)-6-(4-pentylphenyl)-3E-hexene-1,5-diyne | 7% by weight |
| 4-(trans-4-(3-butenyl)cyclohexyl)benzonitrile | 12% by weight |
| 4-(trans-4-(3E-pentenyl)cyclohexyl)benzonitrile | 12% by weight |
| 4-(trans-4-propylcyclohexyl)benzonitrile | 6% by weight |
| 2-(4-ethylpheny)-5-ethyl-1,3-pyrimidine | 4% by weight |
| 2-(4-ethylphenyl)-5-propyl-1,3-pyrimidine | 4% by weight |
| 2-(4-ethylphenyl)-5-butyl-1,3-pyrimidine | 4% by weight |
| 2-(4-fluorophenyl)-5-pentyl-1,3-pyrimidine | 3% by weight |
| 2-(4-ethoxyphenyl)-5-propyl-1,3-pyrimidine | 3% by weight |
| 2-(4-ethoxyphenyl)-5-butyl-1,3-pyrimidine | 3% by weight |
| 1-(4-ethylphenyl)-2-anisylacetylene | 2% by weight |
| 1-(4-propylphenyl)-2-anisylacetylene | 2% by weight |
| 1-(4-butylphenyl)-2-(4-ethoxyphenyl)acetylene | 2% by weight |
| 1-(4-pentylphenyl)-2-anisylacetylene | 2% by weight |
| 1-(4-ethylphenyl)-2-(2-fluoro-4-(trans-4-propylcyclohexyl)phenyl)acetylene | 5% by weight |
| 1-(4-propylphenyl)-2-(2-fluoro-4-trans-4-propylcyclohexyl)phenyl)acetylene | 5% by weight |
| 2-(4-(trans-4-propylcyclohexyl)phenyl)-5-ethyl-1,3-pyrimidine | 3% by weight |
| 2-(4-(trans-4-propylcyclohexyl)phenyl)-5-propyl-1,3-pyrimidine | 3% by weight |
| 2-(4-(trans-4-propylcyclohexyl)phenyl)-5-butyl-1,3-pyrimidine | 3% by weight |
| trans-4-(trans-4-propylcyclohexyl)butylcyclohexane | 8% by weight |

(Production process)

Among the compounds of the present invention, those wherein X=H are obtained by coupling an acetylene derivative of the formula (XI):

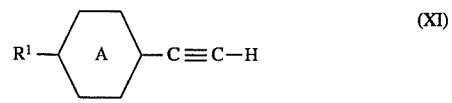

wherein ring A and $R^1$ each are as defined above, to a vinyl chloride derivative expressed by the formula (XII)

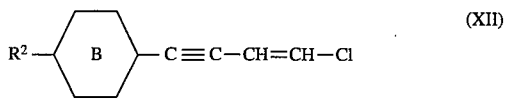

wherein ring B and $R^2$ each are as defined above, in the presence of a transition metal complex catalyst.

This coupling reaction is carried out to the generally known point described in Tetrahedron Letters, Vol. 22, pp 315 (1981). Namely, an acetylene derivative expressed by the formula (XI) is reacted with a vinyl chloride derivative expressed by the formula (XII), by adding a suitable complex catalyst such as those of 10 Group metals or others, and if necessary, a cocatalyst. More concretely, as complex catalysts, it is possible to use a zero valence or divalence palladium complex such as dichlorobistriphenylphosphine palladium, tetrakistriphenylphosphine palladium, palladium acetate, dichlorobis(benzonitrile)palladium (II) complex, etc.

The quantity of the catalyst used depends upon the reactivity of its substrate, and is chosen from within a range of 0.1 to 20% by mol, but a range of 0.5 to 5% by mol is preferable since conversion time is short and side reaction hardly occurs within such a range. As the cocatalyst, it is preferable to use a copper salt such as copper iodide, copper bromide, etc. since it affords a good yield. As the solvent used for the reaction, diethylamine is most general, but besides, there may be used a polar solvent such as triethylamine, pyridine, morphorine, dimethylformamide, etc. or a mixed solvent of the above with a suitable solvent. The reaction temperature of the reaction may be chosen among from a range of $-40°$ C. to a boiling point of the solvent used, but it is preferable to choose a temperature of $0°$ C. to the boiling point of the solvent, since the catalyst activity is well kept and the conversion is high within such a range.

Further, since the reaction active species of the catalyst of the reaction are unstable to air, moisture, etc., it is preferred to carry out the reaction in an inert gas. The thus formed compound of the present invention can be isolated by subjecting it to a usual post-treatment. In particular, in order to remove the complex catalyst remaining in the sysmtem, it is preferred to carry out a purification operation such as distillation, recrystallization, column chromatography or the like. Further, since the coupling reaction advances while the vinyl chloride derivative expressed by the formula (XII) as a raw material retains a specifically steric form in the E-form, the vinyl chloride derivative used is preferred to be in the E-form or a mixture of E-form with Z-form.

Among the compounds used as the raw material, a vinyl chloride derivative expressed by the formula (XII)

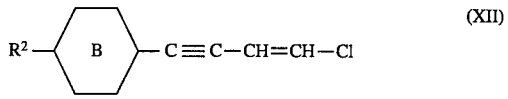

wherein ring B and $R^2$ are as defined above) can be prepared for example according to the following method:

Namely, an acetylene derivative expressed by the formula (XIII)

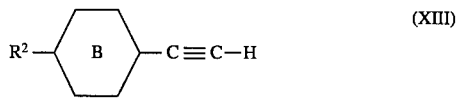

wherein ring B and $R^2$ are as defined above, is coupled to 1,2-dichloroethylene in the presence of a transition metal complex catalyst. This coupling reaction is carried out according to a generally known gist disclosed in the above literature. The details of the reaction are similar to the above reaction of an acetylene derivative with a vinyl chloride derivative; hence the details are ommited.

Further, a compound of the present invention wherein X=F can be prepared according to the following process:

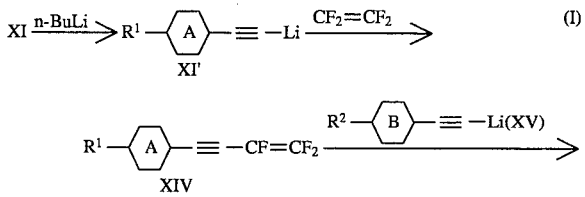

wherein ring A, ring B, $R^1$ and $R^2$ are as defined above.

An acetylene derivative expressed by the formula (XI)

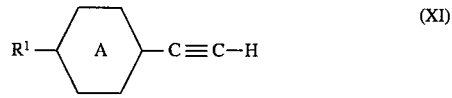

is converted into a Li compound using a base such as butyllithium, followed by treating the compound with tetrafluoroethylene to obtain an intermediate (XIV), and further reacting this (XIV) with a lithium compound, to obtain an aimed compound of the formula (I, X=F).

In more detail, when an acetylene derivative expressed by the formula (XI) is reacted with a base in a suitable solvent, it can be derived into a lithium compound (XI'). A suitable solvent used in this reaction is chosen from among those which do not react with the resulting lithium compound, such as tetrahydrofuran, ether, dimethylformamide, dioxane, dimethylsulfoxide, cyclohexane, hexane, toluene, etc. The reaction temperature of the present invention is generally chosen from among cooled conditions, and room temperature to about $-50°$ C. are preferred in the aspect of simple operation. As the base, commercially available lithium reagents such as n-butyllithium, phenyllithium, methyllithium, lithium isopropylamide, etc. are preferably used in the aspect of good yeild and simple operation. The thus formed compound of the formula (XI') is unstable to conditions of water, oxygen, etc.; hence it is preferred to use the compound in the next reaction without any purification process.

Tetrafluoroethylene is condensed in a cooled flask, followed by dropwise adding thereinto a solution of a lithium compound prepared as above. It is preferred to carry out the reaction at $-78°$ C. to $0°$ C. in the aspect in which the side reaction hardly proceeds. Further, in order to obtain the compound of the formula (XIV) with good efficiency, tetrafluoroethylene is introduced via a means for metering gas such as gas buret. The raw product obtained after the reaction is subjected to the next reaction, as it is, or subjected to conventional post-treatment, whereby it is purified to a sufficient purity as a raw material for the next reaction.

Next, the compound of the formula (XIII) is converted into a lithium compound, in the same manner as that in the compound of the formula (XI), and the resulting compound is reacted with the intermediate (XIV) obtained above. In this case, the reaction system is cooled within a range of $-78°$ C. to $0°$ C., and a solution of the compound of the formula (XV) is dropwise added to the intermediate (XIV) dissolved in a suitable solvent. The solvent used in this reaction is chosen from among those which do not react with the lithium compound (XV) added, such as tetrahydrofuran, ether, dimethylformamide, dioxane, dimethylsulfoxide, cyclohexane, hexane, toluene, etc. After completion of the reaction, by carrying out conventional post-treatment, it is possible to isolate a compound of the formula (I). Further, if necessary, purification is carried out, whereby a purer compound can be obtained.

Further, if the aimed compound of the formula (I) has a symmetric structure, i.e. satisfies the conditions of $R^1=R^2$ and A=B, it is possible to carry out the reaction at one stage, by using an acetylene derivative and butyllithium, each in twice quantity. The reaction conditions, etc. in this case are the same as those in the process of obtaining the above compound of the formula (XIV).

(Effectiveness of the invention)

The compound of the present invention is characterized by having a conjugated hexenediyne structure in its molecule, whereby the compound of the present invention has an incomparably large Δn and has two six-membered rings in its molecule.

Even though the compound is a two ring structure, it is characterized by having a broad liquid crystal temperature range and a low viscosity. Further, the compound of the present invention is sufficiently stable in the environment of its use as liquid crystal element, and no deterioration occurs even under conditions of electromagnetic irradiation, voltage impression, etc. Further, when the compound of the present invention is used as a component of liquid crystal composition, it has a superior compatibility with other liquid crystal materials; hence a novel liquid crystal display element having useful characteristics is effected.

The present invention will be described in more detail by way of Examples, but it should not be construed to be limited thereto.

EXAMPLE 1

Synthesis of
1-(4-ethylphenyl)-6-(4-propylphenyl)-hexa-3E-ene-1,5-diyne

Dichlorobistriphenylphosphinepalladium (350 mg) and copper iodide (50 mg) were placed in a flask and the inside of the system was replaced by argon. A diethylamine solution of 4-ethylphenylacetylene (1.3 g) was added in an argon gas current. A diethylamine solution of trans-1,2-dichloroethylene (1.0 g) was dropwise added with stirring at room temperature. After completion of the dropwise addition, agitation was further carried out at room temperature for 5 hours. After completion of the agitation, water was added to the reaction system and extraction with heptane was carried out. The organic phase was washed with water, followed by drying it over anhydrous magnesium sulfate and concentrating under reduced pressure. The resulting brown oily substance was purified with a silica gel short column, followed by recrystallizing it from ethanol, to obtain colorless solids (1.4 g), which were confirmed to be 1-chloro-4-(4-ethylphenyl)-1E-butene-3-yne as the results of instrumental analysis, etc.

Tetraxistriphenylphosphine palladium (404 mg) and copper iodide (35 mg) were placed in a flask and the inside of the system was replaced by argon, and a diethylamine solution of 1-chloro-4-(4-ethylphenyl)-1E-butene-3-yne (1.4 g) was added in an argon gas current. A diethylamine solution of 4-propylphenylacetylene (1.0 g) was dropwise added with stirring at room temperature. After completion of the dropwise addition, agitation was further carried out at room temperature for 4 hours, followed by adding water to the reaction system and extracting with heptane, washing the organic phase with water, drying it over anhydrous magnesium sulfate, concentrating it under reduced pressure, purifying the resulting brown oily substance with a silica gel short column and recrystallizing from ethanol, to obtain colorless solids (1.1 g), which were confirmed to be the captioned compound as the results of instrumental analysis, etc.

C.80.9°–81.4° C. N.148.0°–148.8° C. I

The following compounds can be prepared in the same manner as in Example 1:

1,6-di(4-ethylphenyl)hexa-3E-ene-1,5-diyne
1-(4-ethylphenyl)-6-(4-butylphenyl)hexa-3E-ene-1,5-diyne
1-(4-ethylphenyl)-6-(4-pentylphenyl)hexa-3E-ene-1,5-diyne
1-(4-ethylphenyl)-6-(4-hexylphenyl)hexa-3E-ene-1,5-diyne
1-(4-ethylphenyl)-6-(4-heptylphenyl)hexa-3E-ene-1,5-diyne
1,6-di(4-propylphenyl)hexa-3E-ene-1,5-diyne
1-(4-propylphenyl)-6-(4-butylphenyl)hexa-3E-ene-1,5-diyne
1-(4-propylphenyl)-6-(4-pentylphenyl)hexa-3E-ene-1,5-diyne
1-(4-propylphenyl)-6-(4-hexylphenyl)hexa-3E-ene-1,5-diyne
1-(4-propylphenyl)-6-(4-heptylphenyl)hexa-3E-ene-1,5-diyne
1,6-di(4-butylphenyl)hexa-3E-ene-1,5-diyne
1-(4-butylphenyl)-6-(4-pentylphenyl)hexa-3E-ene-1,5-diyne
1-(4-butylphenyl)-6-(4-hexylphenyl)hexa-3E-ene-1,5-diyne
1-(4-butylphenyl)-6-(4-heptylphenyl)hexa-3E-ene-1,5-diyne
1,6-di(4-pentylphenyl)hexa-3E-ene-1,5-diyne
1-(4-pentylphenyl)-6-(4-hexylphenyl)hexa-3E-ene-1,5-diyne
1-(4-pentylphenyl)-6-(4-heptylphenyl)hexa-3E-ene-1,5-diyne
1,6-di(4-hexylphenyl)hexa-3E-ene-1,5-diyne
1-(4-hexylphenyl)-6-(4-heptylphenyl)hexa-3E-ene-1,5-diyne
1,6-di(4-heptylphenyl) hexa-3E-ene-1,5-diyne

EXAMPLE 2

Synthesis of
1-(4-propoxyphenyl)-6-(4-ethylphenyl)-hexa-3E-ene-1,5-diyne

Tetraxistriphenylphosphinepalladium (577 mg) and copper iodide (50 mg) were placed in a flask, followed by replacing the inside of the system by argon, adding a diethylamine solution of 1-chloro-4-(4-propoxyphenyl)-1E-butene-3-yne (2.2 g) prepared in the same manner as the above, in an argon current, dropwise adding a diethylamine solution of 4-ethylphenylacetylene (1.3 g) with stirring at room temperature, thereafter agitating at room temperature for 4 hours, thereafter adding water to the reaction system, extracting with heptane, washing the organic phase with water, drying over anhydrous magnesium sulfate, concentrating under reduced pressure, purifying the resulting brown, oily substance with a silica gel short column, and recrystallizing from ethanol, to obtain colorless solids (2.0 g), which were confirmed to be the captioned compound as the results of instrumental analysis, etc.

C.106.3°–106.5° C. N.170.7°–172.0° C. I

The following compounds can be prepared in the same manner as in Example 2:

1-(4-methoxyphenyl)-6-(4-ethylphenyl)hexa-3E-ene-1,5-diyne
1-(4-methoxyphenyl)-6-(4-propylphenyl)hexa-3E-ene-1,5-diyne
1-(4-methoxyphenyl)-6-(4-butylphenyl)hexa-3E-ene-1,5-diyne
1-(4-methoxyphenyl)-6-(4-pentylphenyl)hexa-3E-ene-1,5-diyne
1-(4-methoxyphenyl)-6-(4-hexylphenyl)hexa-3E-ene-1,5-diyne
1-(4-methoxyphenyl)-6-(4-heptylphenyl)hexa-3E-ene-1,5-diyne
1-(4-ethoxyphenyl)-6-(4-ethylphenyl)hexa-3E-ene-1,5-diyne
1-(4-ethoxyphenyl)-6-(4-propylphenyl)hexa-3E-ene-1,5-diyne
1-(4-ethoxyphenyl)-6-(4-butylphenyl)hexa-3E-ene-1,5-diyne
1-(4-ethoxyphenyl)-6-(4-pentylphenyl)hexa-3E-ene-1,5-diyne
1-(4-ethoxyphenyl)-6-(4-hexylphenyl)hexa-3E -ene-1,5-diyne
1-(4-ethoxyphenyl)-6-(4-heptylphenyl)hexa-3E-ene-1,5-diyne
1-(4-propoxyphenyl)-6-(4-propylphenyl)hexa-3E-ene-1,5-diyne
1-(4-propoxyphenyl)-6-(4-butylphenyl)hexa-3E-ene-1,5-diyne
1-(4-propoxyphenyl)-6-(4-pentylphenyl)hexa-3E-ene-1,5-diyne
C.74.6°~75.2° C. N.164.9°~168.5° C. I
1-(4-propoxyphenyl)-6-(4-hexylphenyl)hexa-3E-ene-1,5-diyne
1-(4-propoxyphenyl)-6-(4-heptylphenyl)hexa-3E-ene-1,5-diyne
1-(4-butoxyphenyl)-6-(4-ethylphenyl)hexa-3E-ene-1,5-diyne
1-(4-butoxyphenyl)-6-(4-propylphenyl)hexa-3E-ene-1,5-diyne
1-(4-butoxyphenyl)-6-(4-butylphenyl)hexa-3E-ene-1,5-diyne
1-(4-butoxyphenyl)-6-(4-pentylphenyl)hexa-3E-ene-1,5-diyne
1-(4-butoxyphenyl)-6-(4-hexylphenyl)hexa-3E-ene-1,5-diyne
1-(4-butoxyphenyl)-6-(4-heptylphenyl)hexa-3E-ene-1,5-diyne
1-(4-pentyloxyphenyl)-6-(4-ethylphenyl)hexa-3E-ene-1,5-diyne
1-(4-pentyloxyphenyl)-6-(4-propylphenyl)hexa-3E-ene-1,5-diyne
1-(4-pentyloxyphenyl)-6-(4-butylphenyl)hexa-3E-ene-1,5-diyne
1-(4-pentyloxyphenyl)-6-(4-pentylphenyl)hexa-3E-ene-1,5-diyne
1-(4-pentyloxyphenyl)-6-(4-hexylphenyl)hexa-3E-ene-1,5-diyne
1-(4-pentyloxyphenyl)-6-(4-heptylphenyl)hexa-3E-ene-1,5-diyne
1-(4-hexyloxyphenyl )-6-(4-ethylphenyl)hexa-3E-ene-1,5-diyne
1-(4-hexyloxyphenyl)-6-(4-propylphenyl)hexa-3E-ene-1,5-diyne
1-(4-hexyloxyphenyl)-6-(4-butylphenyl)hexa-3E-ene-1,5-diyne
1-(4-hexyloxyphenyl)-6-(4-pentylphenyl)hexa-3E-ene-1,5-diyne
1-(4-hexyloxyphenyl)-6-(4-hexylphenyl)hexa-3E-ene-1,5-diyne
1-(4-hexyloxyphenyl)-6-(4-heptylphenyl)hexa-3E-ene-1,5-diyne

EXAMPLE 3

Preparation of
1-(trans-4-pentylcyclohexyl)-6-(4-propylphenyl)hexa-3E-ene-1,5-diyne The captioned compound (2.3 g) was prepared from (E)-1-chloro-2-(4-propylphenyl)ethynylethylene (2.0 g) and trans-4-pentylcyclohexylacetylene (1.8 g), in the same manner as in Example 1.

C.75.2°~76.1° C. N.139.4°~140.0° C. I

The following compounds can be prepared in the same manner as in Example 3:

1-(trans-4-ethylcyclohexyl)-6-(4-ethylphenyl)hexa-3E-ene-1,5-diyne
1-(trans-4-ethylcyclohexyl)-6-(4-propylphenyl)hexa-3E-ene-1,5-diyne
1-(trans-4-ethylcyclohexyl)-6-(4-butylphenyl)hexa-3E-ene-1,5-diyne
1-(trans-4-ethylcyclohexyl)-6-(4-pentylphenyl)hexa-3E-ene-1,5-diyne
1-(trans-4-ethylcyclohexyl)-6-(4-hexylphenyl)hexa-3E-ene-1,5-diyne
1-(trans-4-ethylcyclohexyl)-6-(4-heptylphenyl)hexa-3E-ene-1,5-diyne
1-(trans-4-propylcyclohexyl)-6-(4-ethylphenyl )hexa-3E-ene-1,5-diyne
1-(trans-4-propylcyclohexyl)-6-(4-propylphenyl)hexa-3E-ene-1,5-diyne
1-(trans-4-propylcyclohexyl)-6-(4-butylphenyl)hexa-3E-ene-1,5-diyne
1-(trans-4-propylcyclohexyl)-6-(4-pentylphenyl)hexa-3E-ene-1,5-diyne
1-(trans-4-propylcyclohexyl)-6-(4-hexylphenyl)hexa-3E-ene-1,5-diyne
1-(trans-4-propylcyclohexyl)-6-(4-heptylphenyl)hexa-3E-ene-1,5-diyne
1-(trans-4-butylcyclohexyl)-6-(4-ethylphenyl)hexa-3E-ene-1,5-diyne
1-(trans-4-butylcyclohexyl)-6-(4-propylphenyl)hexa-3E-ene-1,5-diyne
1-(trans-4-butylcyclohexyl)-6-(4-butylphenyl)hexa-3E-ene-1,5-diyne
1-(trans-4-butylcyclohexyl)-6-(4-pentylphenyl)hexa-3E-ene-1,5-diyne
1-(trans-4-butylcyclohexyl)-6-(4-hexylphenyl)hexa-3E-ene-1,5-diyne
1-(trans-4-butylcyclohexyl)-6-(4-heptylphenyl)hexa-3E-ene-1,5-diyne
1-(trans-4-pentylcyclohexyl)-6-(4-ethylphenyl)hexa-3E-ene-1,5-diyne
1-(trans-4-pentylcyclohexyl)-6-(4-butylphenyl)hexa-3E-ene-1,5-diyne
1-(trans-4-pentylcyclohexyl)-6-(4-pentylphenyl )hexa-3E-ene-1,5-diyne
1-(trans-4-pentylcyclohexyl)-6-(4-hexylphenyl)hexa-3E-ene-1,5-diyne
1-(trans-4-pentylcyclohexyl)-6-(4-heptylphenyl)hexa-3E-ene-1,5-diyne
1-(trans-4-hexylcyclohexyl)-6-(4-ethylphenyl)hexa-3E-ene-1,5-diyne 1-(trans-4-hexylcyclohexyl)-6-(4-propylphenyl)hexa-3E-ene-1,5-diyne
1-(trans-4-hexylcyclohexyl)-6-(4-butylphenyl)hexa-3E-ene-1,5-diyne
1-(trans-4-hexylcyclohexyl)-6-(4-pentylphenyl)hexa-3E-ene-1,5-diyne
1-(trans-4-hexylcyclohexyl)-6-(4-hexylphenyl)hexa-3E-ene-1,5-diyne
1-(trans-4-hexylcyclohexyl)-6 -(4-heptylphenyl)hexa-3E-ene-1,5-diyne
1-(trans-4-heptylcyclohexyl)-6-(4-ethylphenyl)hexa-3E-ene-1,5-diyne
1-(trans-4-heptylcyclohexyl)-6-(4-propylphenyl)hexa-3E-ene-1,5-diyne
1-(trans-4-heptylcyclohexyl)-6 -(4-butylphenyl)hexa-3E-ene-1,5-diyne

EXAMPLE 4

Preparation of
1-(trans-4-ethylcyclohexyl)-6-(trans-4-propylcyclohexyl)hexa-3E-ene-1,5-diyne The captioned compound (2.3 g) was prepared from (E)-1-chloro-2-(trans-4-propylcyclohexyl)ethynylethylene (2.1 g) and trans-4-pentylcyclohexylacetylene (1.8 g), in the same manner as in Example 1.

The following compounds can be prepared in the same manner as in Example 4:
1,6-di(trans-4-ethylcyclohexyl)hexa-3E-ene-1,5-diyne
1-(trans-4-ethylcyclohexyl)-6-(trans-4-butylcyclohexyl)hexa-3E-ene-1,5-diyne
1-(trans-4-ethylcyclohexyl)-6-(trans-4-pentylcyclohexyl)hexa-3E-ene-1,5-diyne
1-(trans-4-ethylcyclohexyl)-6-(trans-4-hexylcyclohexyl)hexa-3E-ene-1,5-diyne
1-(trans-4-ethylcyclohexyl)-6-(trans-4-heptylcyclohexyl)hexa-3E-ene-1,5-diyne
1,6-di(trans-4-propylcyclohexyl)hexa-3E-ene-1,5-diyne
1-(trans-4-propylcyclohexyl)-6-(trans-4-butylcyclohexyl)hexa-3E-ene-1,5-diyne
1-(trans-4-propylcyclohexyl)-6-(trans-4-pentylcyclohexyl)hexa-3E-ene-1,5-diyne
1-(trans-4-propylcyclohexyl)-6-(trans-4-hexylcyclohexyl)hexa-3E-ene-1,5-diyne
1-(trans-4-propylcyclohexyl)-6-(trans-4-heptylcyclohexyl)hexa-3E-ene-1,5-diyne
1,6-di(trans-4-butylcyclohexyl)hexa-3E-ene-1,5-diyne
1-(trans-4-butylcyclohexyl)-6-(trans-4-pentylcyclohexyl)hexa-3E-ene-1,5-diyne
1-(trans-4-butylcyclohexyl)-6-(trans-4-hexylcyclohexyl)hexa-3E-ene-1,5-diyne
1-(trans-4-butylcyclohexyl)-6-(trans-4-heptylcyclohexyl)hexa-3E-ene-1,5-diyne
1,6-di(trans-4-pentylcyclohexyl)hexa-3E-ene-1,5-diyne
1-(trans-4-pentylcyclohexyl)-6-(trans-4-hexylcyclohexyl)hexa-3E-ene-1,5-diyne
1-(trans-4-pentylcyclohexyl)-6-(trans-4-heptylcyclohexyl)hexa-3E-ene-1,5-diyne
1,6-di(trans-4-hexylcyclohexyl)hexa-3E-ene-1,5-diyne
1-(trans-4-hexylcyclohexyl)-6-(trans-4-heptylcyclohexyl)hexa-3E-ene-1,5-diyne
1,6-di(trans-4-heptylcyclohexyl)hexa-3E-ene-1,5-diyne

EXAMPLE 5

Preparation of
3,4-difluoro-1,6-di(4-propylphenyl)hexa-3E-ene-1,5-diyne

4-Propylphenylacetylene (2.9 g) was placed in a flask, followed by adding tetrahydrofuran, adding n-butyllithium (12.5 ml, 1.6M hexane solution) while cooling at 0° C. with stirring, agitating the reaction mixture at the same temperature for 30 minutes, transferring it to a dropping funnel in nitrogen gas current, introducing tetrafluoroethylene (220 ml) into a flask cooled down to −78° C. through a gas burette, dropwise adding lithium acetylide prepared above from a dropping funnle at the same temperature with stirring, elevating the temperature of the reaction solution up to room temperature, further agitating it for 30 minutes, adding ice water to the reaction solution, extracting it with ether, washing the organic phase with water, concentrating it under reduced pressure, to obtain an yellow oily substance, purifying it with a silica gel short column to obtain white solids, and recrystallizing from ethanol, to obtain white solids (2.5 g), which were confirmed to be the captioned compound at the results of instrumental analysis, etc.

C.89.8°~90.0° C. N.144.1°~145.1° C. I

The following compounds can be prepared in the same manner as the above:
3,4-difluoro-1,6-di(4-ethylphenyl)hexa-3E-ene-1,5-diyne
3,4-difluoro-1,6-di(4-butylphenyl)hexa-3E-ene-1,5-diyne
3,4-difluoro-1,6-di(4-pentylphenyl)hexa-3E-ene-1,5-diyne
3,4-difluoro-1,6-di(4-hexylphenyl)hexa-3E-ene-1,5-diyne
3,4-difluoro-1,6-di(4-heptylphenyl)hexa-3E-ene-1,5-diyne

EXAMPLE 6

Preparation of
3,4-difluoro-1-(4-propoxyphenyl)-6-(4-propylphenyl)hexa-3E-ene-1,5-diyne 4-Propylphenylacetylene (1.4 g) was placed in a flask, followed by adding tetrahydrofuran, cooling the mixture at 0° C., adding n-butyllithium (6.3 ml, 1.6M hexane solution) with stirring, agitating the reaction system at the same temperature for 30 minutes, transferring it into a dropping funnel in nitrogen gas current, introducing tetrahydrofuran (220 ml) into a flask cooled down to −78° C. through a gas burette, dropwise adding the lithium acetylide prepared above, at the same temperature with stirring, elevating the temperature of the reaction solution up to room temperature, further agitating for 30 minutes, again cooling the reaction solution down to −78° C., dropwise adding a tetrahydrofuran solution of lithium acetylide prepared from propoxyphenylacetylene (1.6 g) and n-butyllithium (6.3 ml, 1.6M hexane solution), elevating the temperature of the reaction solution up to room temperature, further agitating it for 30 minutes, adding ice water, extracting with ether, washing with water, drying, concentrating under reduced pressure, isolating and purifying the resulting oily substance with a silica gel column chromatography to obtain white solids, and recrystallizing them from ethanol to obtain white crystals of the captioned compound.

The following compounds can be prepared in the same manner as in Example 6:
3,4-difluoro-1-(4-methoxyphenyl)-6-(4-ethylphenyl)hexa-3E-ene-1,5-diyne
3,4-difluoro-1-(4 -methoxyphenyl)-6-(4-propylphenyl)hexa-3E-ene-1,5-diyne
3,4-difluoro-1-(4-methoxyphenyl)-6-(4-butylphenyl)hexa-3E-ene-1,5-diyne
3,4-difluoro-1-(4-methoxyphenyl)-6-(4-pentylphenyl)hexa-3E-ene-1,5-diyne
3,4-difluoro-1-(4-methoxyphenyl)-6-(4-hexylphenyl)hexa-3E-ene-1,5-diyne
3,4-difluoro-1-(4-methoxyphenyl)-6-(4-heptylphenyl)hexa-3E-ene-1,5-diyne 3,4-difluoro-1-(4-ethoxyphenyl)-6-(4-ethylphenyl)hexa-3E-ene-1,5-diyne
3,4-difluoro-1-(4-ethoxyphenyl)-6-(4-propylphenyl)hexa-3E-ene-1,5-diyne
3,4-difluoro-1-(4-ethoxyphenyl)-6-(4-butylphenyl)hexa-3E-ene-1,5-diyne
3,4-difluoro-1-(4-ethoxyphenyl)-6-(4-pentylphenyl)hexa-3E-ene-1,5-diyne
3,4-difluoro-1-(4-ethoxyphenyl)-6-(4-hexylphenyl)hexa-3E-ene-1,5-diyne
3,4-difluoro-1-(4-ethoxyphenyl)-6-(4-heptylphenyl)hexa-3E-ene-1,5-diyne
3,4-difluoro-1-(4-propoxyphenyl)-6-(4-ethylphenyl)hexa-3E-ene-1,5-diyne
3,4-difluoro-1-(4-propoxyphenyl)-6-(4-butylphenyl)hexa-3E-ene-1,5-diyne
3,4-difluoro-1-(4-propoxyphenyl)-6-(4-pentylphenyl)hexa-3E-ene-1,5-diyne
3,4-difluoro-1-(4-propoxyphenyl)-6-(4-hexylphenyl)hexa-3E-ene-1,5-diyne
3,4-difluoro-1-(4-propoxyphenyl)-6-(4-heptylphenyl)hexa-3E-ene-1,5-diyne
3,4-difluoro-1-(4-butylphenyl)-6-(4-ethylphenyl)hexa-3E-ene-1,5-diyne
3,4-difluoro-1-(4-butoxyphenyl)-6-(4-propylphenyl)hexa-3E-ene-1,5-diyne
3,4-difluoro-1-(4-butoxyphenyl)-6-(4-butylphenyl)hexa-3E-ene-1,5-diyne
3,4-difluoro-1-(4-butoxyphenyl)-6-(4-pentylphenyl)hexa-3E-ene-1,5-diyne
3,4-difluoro-1-(4-butoxyphenyl)-6-(4-hexylphenyl)hexa-3E-ene-1,5-diyne
3,4-difluoro-1-(4-butoxyphenyl)-6-(4-heptylphenyl)hexa-3E-ene-1,5-diyne
3,4-difluoro-1-(4-pentyloxyphenyl)-6-(4-ethylphenyl)hexa-3E-ene-1,5-diyne
3,4-difluoro-1-(4-pentyloxyphenyl)-6-(4-propylphenyl)hexa-3E-ene-1,5-diyne
3,4-difluoro-1-(4-pentyloxyphenyl)-6-(4-butylphenyl)hexa-3E-ene-1,5-diyne
3,4-difluoro-1-(4-pentyloxyphenyl)-6-(4-pentylphenyl)hexa-3E-ene-1,5-diyne
3,4-difluoro-1-(4-pentyloxyphenyl)-6-(4-hexylphenyl)hexa-3E-ene-1,5-diyne
3,4-difluoro-1-(4-pentyloxyphenyl)-6-(4-heptylphenyl)hexa-3E-ene-1,5-diyne
3,4-difluoro-1-(4-hexyloxyphenyl)-6-(4-ethylphenyl)hexa-3E-ene-1,5-diyne
3,4-difluoro-1-(4-hexyloxyphenyl)-6-(4-propylphenyl)hexa-3E-ene-1,5-diyne
3,4-difluoro-1-(4-hexyloxyphenyl)-6-(4-butylphenyl)hexa-3E-ene-1,5-diyne
3,4-difluoro-1-(4-hexyloxyphenyl )-6-(4-pentylphenyl)hexa-3E-ene-1,5-diyne
3,4-difluoro-1-(4-hexyloxyphenyl )-6-(4-hexylphenyl)hexa-3E-ene-1,5-diyne
3,4-difluoro-1-(4-hexyloxyphenyl)-6-(4-heptylphenyl)hexa-3E-ene-1,5-diyne
3,4-difluoro-1-(4-ethylphenyl)-6-(4-propylphenyl)hexa-3E-ene-1,5-diyne
3,4-difluoro-1-(4-ethylphenyl)-6-(4-butylphenyl)hexa-3E-ene-1,5-diyne
3,4-difluoro-1-(4-ethylphenyl)-6-(4-pentylphenyl)hexa-3E-ene-1,5-diyne
3,4-difluoro-1-(4-ethylphenyl)-6-(4-hexylphenyl)hexa-3E-ene-1,5-diyne
3,4-difluoro-1-(4-ethylphenyl)-6-(4-heptylphenyl)hexa-3E-ene-1,5-diyne
3,4-difluoro-1-(4 -propylphenyl)-6-(4-butylphenyl)hexa-3E-ene-1,5-diyne
3,4-difluoro-1-(4-propylphenyl)-6-(4-pentylphenyl)hexa-3E-ene-1,5-diyne
3,4-difluoro-1-(4-propylphenyl)-6-(4-hexylphenyl)hexa-3E-ene-1,5-diyne
3,4-difluoro-1-(4-propylphenyl)-6-(4-heptylphenyl)hexa-3E-ene-1,5-diyne
3,4-difluoro-1-(4-butylphenyl)-6-(4-pentylphenyl)hexa-3E-ene-1,5-diyne
3,4-difluoro-1-(4-butylphenyl )-6-(4-hexylphenyl)hexa-3E-ene-1,5-diyne
3,4-difluoro-1-(4-butylphenyl)-6-(4 -heptylphenyl)hexa-3E-ene-1,5-diyne
3,4-difluoro-1-(4-pentylphenyl)-6-(4-hexylphenyl)hexa-3E-ene-1,5-diyne
3,4-difluoro-1-(4-pentylphenyl )-6 -(4-heptylphenyl)hexa-3E-ene-1,5-diyne
3,4-difluoro-1-(4-hexylphenyl)-6-(4-heptylphenyl)hexa-3E-ene-1,5-diyne

EXAMPLE 7

Preparation of
1-(trans-4-pentylcyclohexyl)-6-(4-propoxyphenyl)
hexa-3E-ene-1,5-diyne The captioned compound (2.4 g) was prepared from (E)-1-chloro-2-(4-propoxyphenyl) ethynylethylene (2.2 g) and trans-4-pentylcyclohexylacetylene (1.8 g), in the same manner as in Example 1.

The following compounds can be prepared in the same manner as in Example 7:
1-(trans-4-ethylcyclohexyl)-6-(4-ethoxyphenyl)hexa-3E-ene-1,5-diyne
1-(trans -4-ethylcyclohexyl)-6-(4-propoxyphenyl)hexa-3E-ene-1,5-diyne
1-(trans-4-ethylcyclohexyl)-6-(4-butoxyphenyl)hexa-3E-ene-1,5-diyne
1-(trans-4-ethylcyclohexyl)-6-(4-pentyloxyphenyl)hexa-3E-ene-1,5-diyne
1-(trans-4-ethylcyclohexyl)-6-(4-hexyloxyphenyl)hexa-3E-ene-1,5-diyne
1-(trans-4-ethylcyclohexyl)-6-(4-heptyloxyphenyl)hexa-3E-ene-1,5-diyne
1-(trans-4-propylcyclohexyl)-6-(4-ethoxyphenyl)hexa-3E-ene-1,5-diyne
1-(trans-4-propylcyclohexyl)-6-(4-propoxyphenyl)hexa-3E-ene-1,5 -diyne
1-(trans-4-propylcyclohexyl)-6-(4-butoxyphenyl)hexa-3E-ene-1,5-diyne
1-(trans-4-propylcyclohexyl)-6-(4-pentyloxyphenyl)hexa-3E-ene-1,5-diyne
1-(trans-4-propylcyclohexyl)-6-(4-hexyloxyphenyl)hexa-3E-ene-1,5-diyne
1-(trans-4-propylcyclohexyl)-6-(4-heptyloxyphenyl)hexa-3E-ene-1,5-diyne
1-(trans-4-butylcyclohexyl)-6-(4-ethoxyphenyl)hexa-3E-ene-1,5-diyne
1-(trans-4-butylcyclohexyl)-6-(4-propoxyphenyl)hexa-3E-ene-1,5-diyne
1-(trans-4-butylcyclohexyl)-6-(4-butoxyphenyl)hexa-3E-ene-1,5 -diyne
1-(trans-4-butylcyclohexyl)-6-(4-pentyloxyphenyl)-hexa-3E-ene-1,5-diyne
1-(trans-4-butylcyclohexyl)-6-(4-hexyloxyphenyl)hexa-3E-ene-1,5-diyne 1-(trans-4-butylcyclohexyl)-6-(4-heptyloxyphenyl)-hexa-3E-ene-1,5-diyne
1-(trans-4-pentylcyclohexyl)-6-(4-ethoxyphenyl)hexa-3E-ene-1,5-diyne
1-(trans-4-pentylcyclohexyl)-6-(4-butoxyphenyl)hexa-3E-ene-1,5-diyne
1-(trans-4-pentylcyclohexyl)-6-(4-pentyloxyphenyl)hexa-3E-ene-1,5-diyne
1-(trans-4-pentylcyclohexyl)-6-(4-hexyloxyphenyl)hexa-3E-ene-1,5-diyne
1-(trans-4-pentylcyclohexyl)-6-(4-heptyloxyphenyl)hexa-3E-ene-1,5-diyne
1-(trans-4-hexylcyclohexyl)-6-(4-ethoxyphenyl)hexa-3E-ene-1,5-diyne
1-(trans-4-hexylcyclohexyl)-6-(4-propoxyphenyl)hexa-3E-ene-1,5-diyne
1-(trans-4-hexylcyclohexyl)-6-(4-butoxyphenyl)hexa-3E-ene-1,5-diyne
1-(trans-4-hexylcyclohexyl)-6-(4-pentyloxyphenyl)hexa-3E-ene-1,5-diyne
1-(trans-4-hexylcyclohexyl)-6-(4-hexyloxyphenyl)hexa-3E-ene-1,5-diyne
1-(trans-4-hexylcyclohexyl)-6-(4-heptyloxyphenyl)hexa-3E-ene-1,5-diyne
1-(trans-4-heptylcyclohexyl)-6-(4-ethoxyphenyl)hexa-3E-ene-1,5-diyne
1-(trans-4-heptylcyclohexyl)-6-(4-propoxyphenyl)hexa-3E-ene-1,5-diyne
1-(trans-4-heptylcyclohexyl)-6-(4-butoxyphenyl)hexa-3E-ene-1,5-diyne
1-(trans-4-heptylcyclohexyl)-6-(4-pentyloxyphenyl)hexa-3E-ene-1,5-diyne
1-(trans-4-heptylcyclohexyl)-6-(4-hexyloxyphenyl)hexane-3E-ene-1,5-diyne
1-(trans-4-heptylcyclohexyl)-6-(4-heptyloxyphenyl)hexane-3E-ene-1,5-diyne

What we claim is:

1. A hexenediyne having the following formula (I):

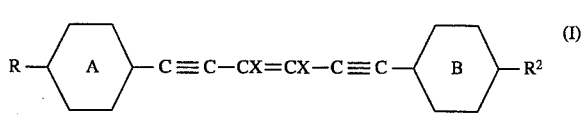

(I)

wherein $R^1$ and $R^2$ each represents an alkyl group of 1 to 10 carbon atoms or an alkoxy group of 1 to 10 carbon atoms independently of each other; ring A and ring B each represents 1,4-cyclohexylene or 1,4-phenylene independently of each other; and X represents hydrogen atom or fluorine atom.

2. A compound according to claim 1, wherein ring A represents 1,4-cyclohexylene.

3. A compound according to claim 1 wherein ring A represents 1,4-phenylene and X represents hydrogen atom.

4. A compound according to claim 1 wherein ring A represents 1,4-phenylene and X represents fluorine atom.

5. A compound according to claim 3 wherein ring B represents 1,4-phenylene.

6. A compound according to claim 3 wherein $R^1$ and $R^2$ each represent an alkyl group of 1 to 10 carbon atoms and ring B represents 1,4-phenylene.

7. A compound according to claim 3 wherein $R^1$ represents an alkoxy group of 1 to 10 carbon atoms; $R^2$ represents an alkyl group of 1 to 10 carbon atoms; and ring B represents 1,4-phenylene.

8. A compound according to claim 3 wherein ring B represents 1,4-cyclohexylene.

9. A compound according to claim 2 wherein ring B represents 1,4-cyclohexylene and X represents hydrogen atom.

10. A compound according to claim 4 wherein ring B represents 1, 4-phenylene.

11. A compound according to claim 4 wherein $R^1$ and $R^2$ each represent an alkyl group of 1 to 10 carbon atoms and ring B represents 1,4-phenylene.

12. A compound according to claim 4 wherein $R^1$ represents an alkoxy group of 1 to 10 carbon atoms; $R^2$ represents an alkyl group of 1 to 10 carbon atoms; and ring B represents 1,4-phenylene.

13. A liquid crystal composition which is characterized by containing at least one kind of liquid crystalline compounds expressed by the formula I of the claim 1.

14. A liquid crystal composition which is characterized by containing as a first component, at least one compound of Formula I of claim 1, and as a second component, at least one compound selected from the group consisting of those expressed by the following formulas II, III and IV:

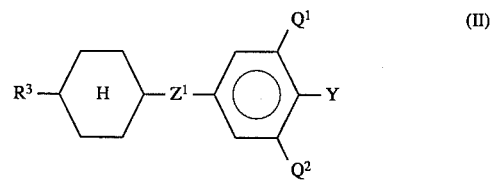

(II)

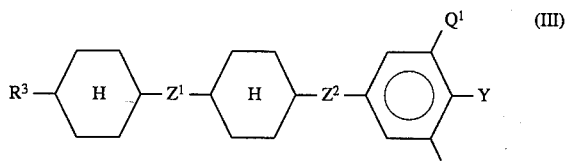

(III)

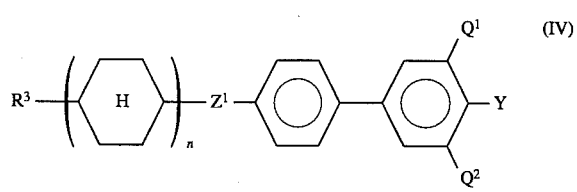

(IV)

wherein $R^3$ represents an alkyl group of 1 to 10 carbon atoms; Y represents F or Cl; $Q^1$ and $Q^2$ each represents H or F independently of each other; n represents 1 or 2; and $Z^1$ and $Z^2$ each represents —$CH_2CH_2$— or a covalent bond, independently of each other.

15. A liquid crystal composition which is characterized by containing as a first component, at least one compound of Formula I of claim 1, and as a second component, at least one compound selected from the group consisting of those expressed by the following formulas V, VI, VII, VIII and IX:

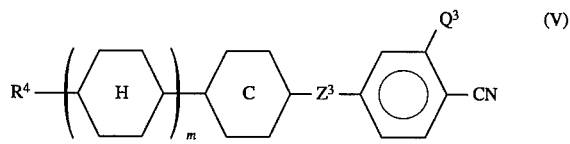

(V)

wherein $R^4$ represents an alkyl group of 1 to 10 carbon atoms or an alkenyl group of 2 to 10 carbon atoms, and in either of the groups, optionally one or more non-adjacent methylene groups (—$CH_2$—) may be replaced by oxygen atom(s) (—O—); $Z^3$ represents —$CH_2CH_2$—, —COO— or covalent bond; $Q^3$ represents H or F; ring C represents 1,4-cyclohexylene, 1,4-phenylene or 1,3-dioxane-2,5-diyl; and m represents 0 or 1,

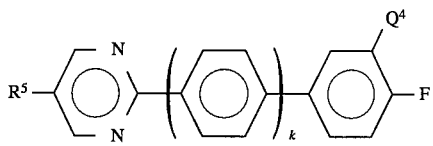

wherein $R^5$ represents an alkyl group of 1 to 10 carbon atoms; $Q^4$ represents H or F; and k represents 0 or 1,

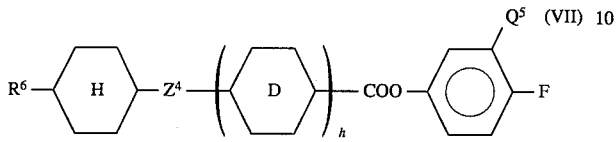

wherein $R^6$ represents an alkyl group of 1 to 10 carbon atoms; ring D represents 1,4-cyclohexylene or 1,4-phenylene; $Q^5$ represents H or F; $Z^4$ represents —COO— or covalent bond; and h represents 0 or 1,

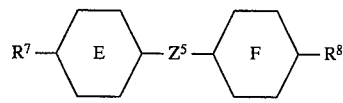

wherein $R^7$ and $R^8$ each represents an alkyl group of 1 to 10 carbon atoms or an alkenyl group of 2 to 10 carbon atoms, independently of each other, and in either of the groups, optionally one or more non-adjacent methylene groups (—$CH_2$—) may be replaced by oxygen atom(s) (—O—); ring E represents 1,4-cyclohexylene, 1,3-pyrimidine-2,5-diyl or 1,4-phenylene; ring F represents 1,4-cyclohexylene or 1,4-phenylene, and $Z^5$ represents —C≡C—, —COO—, —$CH_2CH_2$— or covalent bond, and

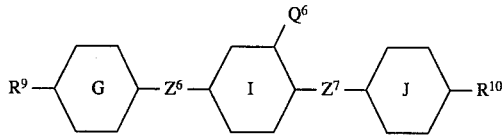

wherein $R^9$ represents an alkyl group or an alkoxy group, each of 1 to 10 carbon atoms; $R^{10}$ represents an alkyl group, an alkoxy group or an alkoxymethyl group, each 1 to 10 carbon atoms; ring G represents 1,4-cyclohexylene or 1,3-pyrimidine-2,5-diyl; ring I and ring J each represent 1,4-cyclohexylene or 1,4-phenylene, independently of each other, $Z^6$ represents —COO—, —$CH_2CH_2$— or covalent bond; $Z^7$ represents —C≡C—, —COO— or covalent bond; and $Q^6$ represents H or F.

16. A liquid crystal composition which is characterized by containing as a first component, at least one compound of Formula I, and as a second component, at least one compound chosen from among those expressed by the formulas II, III and IV, all as set forth in claim 14, and as a third component, at least one compound chosen from among those expressed by the following formulas V, VI, VII, VIII and IX:

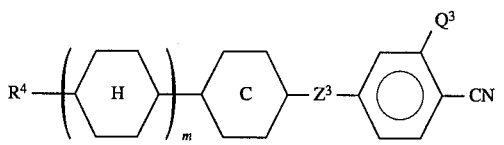

wherein $R^4$ represents an alkyl group of 1 to 10 carbon atoms or an alkenyl group of 2 to 10 carbon atoms, and in either of the groups, optionally one or more non-adjacent methylene groups (—$CH_2$—) may be replaced by oxygen atom(s) (—O—); $Z^3$ represents —$CH_2CH_2$—, —COO— or covalent bond; $Q^3$ represents H or F; ring C represents 1,4-cyclohexylene, 1,4-phenylene or 1,3-dioxane-2,5-diyl; and m represents 0 or 1,

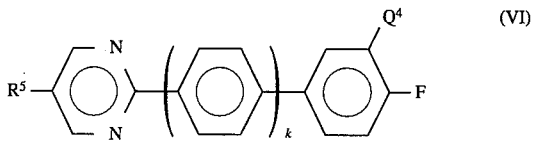

wherein $R^5$ represents an alkyl group of 1 to 10 carbon atoms; $Q^4$ represents H or F; and k represents 0 or 1,

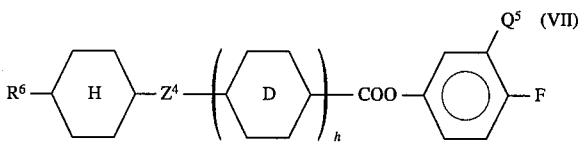

wherein $R^6$ represents an alkyl group of 1 to 10 carbon atoms; ring D represents 1,4-cyclohexylene or 1,4-phenylene; $Q^5$ represents H or F; $Z^4$ represents —COO— or covalent bond; and h represents 0 or 1,

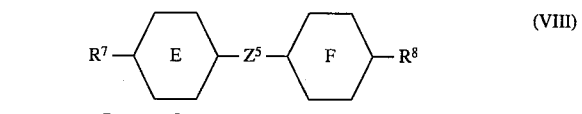

wherein $R^7$ and $R^8$ each represents an alkyl group of 1 to 10 carbon atoms or an alkenyl group of 2 to 10 carbon atoms, independently of each other, and in either of the groups, optionally one or more non-adjacent methylene groups (—$CH_2$—) may be replaced by oxygen atom(s) (—O—); ring E represents 1,4-cyclohexylene, 1,3-pyrimidine-2,5-diyl or 1,4-phenylene; ring F represents 1,4-cyclohexylene or 1,4-phenylene, and $Z^5$ represents —C≡C—, —COO—, —$CH_2CH_2$— or covalent bond, and

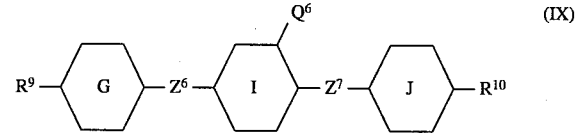

wherein $R^9$ represents an alkyl group or an alkoxy group, each of 1 to 10 carbon atoms; $R^{10}$ represents an alkyl group, an alkoxy group or an alkoxymethyl group, each 1 to 10 carbon atoms; ring G represents 1,4-cyclohexylene or 1,3-pyrimidine-2,5-diyl; ring I and ring J each represent 1,4-cyclohexylene or 1,4-phenylene, independently of each other, $Z^6$ represents —COO—, —$CH_2CH_2$— or covalent bond; $Z^7$ represents —C≡C—, —COO— or covalent bond; and $Q^6$ represents H or F.

17. A liquid crystal display element comprising a liquid crystal composition as set forth in claim 13.

18. A liquid crystal display element comprising a liquid crystal composition as set forth in claim 14.

19. A liquid crystal display element comprising a liquid crystal composition as set forth in claim 15.

20. A liquid crystal display element comprising a liquid crystal composition as set forth in claim 16.

* * * * *